US008764765B2

(12) United States Patent
Piskun et al.

(10) Patent No.: US 8,764,765 B2
(45) Date of Patent: *Jul. 1, 2014

(54) LAPAROSCOPIC INSTRUMENT AND RELATED SURGICAL METHOD

(75) Inventors: Gregory Piskun, Morganville, NJ (US); Oleg Shikhman, Trumbull, CT (US); Anatoly Konik, Haifa (IL); Dan Rottenberg, Haifa (IL); Christopher Battles, Seymour, CT (US); Michael Abrams, New Haven, CT (US); Jeffrey Radziunas, Wallingford, CT (US); Danial Ferreira, Milford, CT (US)

(73) Assignee: Covidien LP, Mansfield, MA (US)

( * ) Notice: Subject to any disclaimer, the term of this patent is extended or adjusted under 35 U.S.C. 154(b) by 631 days.

This patent is subject to a terminal disclaimer.

(21) Appl. No.: 12/550,617

(22) Filed: Aug. 31, 2009

(65) Prior Publication Data
US 2010/0057121 A1 Mar. 4, 2010

Related U.S. Application Data

(63) Continuation-in-part of application No. 10/895,546, filed on Jul. 21, 2004, now Pat. No. 7,753,901, and a continuation-in-part of application No. 10/668,542, filed on Sep. 23, 2003, now Pat. No. 7,850,600.

(60) Provisional application No. 61/191,733, filed on Sep. 11, 2008.

(51) Int. Cl.
*A61B 1/04* (2006.01)
*A61F 11/00* (2006.01)

(52) U.S. Cl.
USPC .................. 606/108; 600/112; 600/204

(58) Field of Classification Search
USPC .................. 604/539, 523, 528, 533, 174–75, 604/164.01, 164.04, 164.07, 164.09, 604/165.01, 165.02, 165.04; 606/108
See application file for complete search history.

(56) References Cited

U.S. PATENT DOCUMENTS

| 2,669,991 A | 2/1954 | Curutchet |
| 3,299,883 A | 1/1967 | Rubens |
| 3,583,710 A | 6/1971 | Burelle et al. |
| 4,016,884 A | 4/1977 | Kwan-Gett |

(Continued)

FOREIGN PATENT DOCUMENTS

| EP | 0567146 | 10/1993 |
| EP | 0592244 | 4/1994 |

(Continued)

OTHER PUBLICATIONS

International Search Report for PCT/US05/24636 dated Jun. 20, 2006. (2 pages).

(Continued)

*Primary Examiner* — Kevin C Sirmons
*Assistant Examiner* — Andrew Gilbert

(57) ABSTRACT

A medical instrument insertable through a cannula, the instrument comprising an elongate shaft; and an operative tip having a first jaw and a second jaw movable with respect to the first jaw. The operative tip disposed at a distal end of said elongate shaft and being disposed on said shaft for rotation relative to at least a distal end portion of said shaft about a longitudinal axis of said distal end portion.

18 Claims, 30 Drawing Sheets

(56) References Cited

U.S. PATENT DOCUMENTS

| | | |
|---|---|---|
| 4,112,932 A | 9/1978 | Chiulli |
| 4,309,994 A | 1/1982 | Grunwald |
| 4,538,594 A | 9/1985 | Boebel et al. |
| 4,608,965 A | 9/1986 | Anspach, Jr. et al. |
| 4,644,951 A | 2/1987 | Bays |
| 4,863,430 A | 9/1989 | Klyce et al. |
| 4,863,438 A | 9/1989 | Gauderer et al. |
| 5,026,366 A | 6/1991 | Leckrone |
| 5,159,921 A | 11/1992 | Hoover |
| 5,183,471 A | 2/1993 | Wilk |
| 5,241,968 A | 9/1993 | Slater |
| 5,242,409 A | 9/1993 | Buelna |
| 5,258,006 A | 11/1993 | Rydell et al. |
| 5,269,772 A | 12/1993 | Wilk |
| 5,312,391 A | 5/1994 | Wilk |
| 5,330,486 A | 7/1994 | Wilk |
| 5,334,143 A | 8/1994 | Carroll |
| 5,366,478 A | 11/1994 | Brinkerhoff et al. |
| 5,375,588 A | 12/1994 | Yoon |
| 5,383,852 A | 1/1995 | Stevens-Wright |
| 5,391,156 A | 2/1995 | Hildwein et al. |
| 5,395,327 A | 3/1995 | Lundquist et al. |
| 5,395,367 A | 3/1995 | Wilk |
| 5,441,483 A | 8/1995 | Avitall |
| 5,467,763 A | 11/1995 | McMahon et al. |
| 5,480,410 A | 1/1996 | Cuschieri et al. |
| 5,490,843 A | 2/1996 | Hildwein et al. |
| 5,509,893 A | 4/1996 | Pracas |
| 5,522,791 A | 6/1996 | Leyva |
| 5,540,648 A | 7/1996 | Yoon |
| 5,545,179 A | 8/1996 | Williamson, IV |
| 5,549,563 A | 8/1996 | Kronner |
| 5,549,637 A | 8/1996 | Crainich |
| 5,571,115 A | 11/1996 | Nicholas |
| 5,571,137 A | 11/1996 | Marlow et al. |
| 5,575,799 A | 11/1996 | Bolanos et al. |
| 5,578,048 A | 11/1996 | Pasqualucci et al. |
| 5,603,723 A | 2/1997 | Aranyi et al. |
| 5,634,911 A | 6/1997 | Hermann et al. |
| 5,634,937 A | 6/1997 | Mollenauer et al. |
| 5,651,771 A | 7/1997 | Tangherlini et al. |
| 5,653,705 A | 8/1997 | de la Torre et al. |
| 5,662,662 A | 9/1997 | Bishop et al. |
| 5,672,168 A | 9/1997 | de la Torre et al. |
| 5,683,378 A | 11/1997 | Christy |
| 5,725,536 A | 3/1998 | Oberlin et al. |
| 5,735,791 A | 4/1998 | Alexander, Jr. et al. |
| 5,782,859 A | 7/1998 | Nicholas et al. |
| 5,803,921 A | 9/1998 | Bonadio |
| 5,830,191 A | 11/1998 | Hildwein et al. |
| 5,836,871 A | 11/1998 | Wallace et al. |
| 5,857,461 A | 1/1999 | Levitsky et al. |
| 5,860,995 A * | 1/1999 | Berkelaar ............... 606/174 |
| 5,871,474 A | 2/1999 | Hermann et al. |
| 5,904,703 A | 5/1999 | Gilson |
| 5,906,577 A | 5/1999 | Beane et al. |
| 5,916,147 A | 6/1999 | Boury |
| 5,916,198 A | 6/1999 | Dillow |
| 5,931,832 A | 8/1999 | Jensen |
| 5,957,913 A | 9/1999 | de la Torre et al. |
| 5,964,781 A | 10/1999 | Mollenauer et al. |
| 5,997,515 A | 12/1999 | de la Torre et al. |
| 6,018,094 A | 1/2000 | Fox |
| 6,024,736 A | 2/2000 | de la Torre et al. |
| 6,033,378 A | 3/2000 | Lundquist et al. |
| 6,033,426 A | 3/2000 | Kaji |
| 6,042,573 A | 3/2000 | Lucey |
| 6,077,288 A | 6/2000 | Shimomura et al. |
| 6,086,603 A | 7/2000 | Termin et al. |
| 6,099,506 A | 8/2000 | Macoviak et al. |
| 6,142,936 A | 11/2000 | Beane et al. |
| 6,217,555 B1 | 4/2001 | Hart et al. |
| 6,217,590 B1 | 4/2001 | Levinson |
| 6,238,373 B1 | 5/2001 | de la Torre et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence |
| 6,537,209 B1 | 3/2003 | Pinkhasik et al. |
| 6,551,270 B1 | 4/2003 | Bimbo et al. |
| 6,558,371 B2 | 5/2003 | Dorn |
| 6,578,577 B2 | 6/2003 | Bonadio et al. |
| 6,582,364 B2 | 6/2003 | Butler et al. |
| 6,623,426 B2 | 9/2003 | Bonadio et al. |
| 6,669,674 B1 | 12/2003 | Macoviak et al. |
| 6,676,639 B1 | 1/2004 | Ternström |
| 6,706,050 B1 | 3/2004 | Giannadakis |
| 6,800,084 B2 | 10/2004 | Davison et al. |
| 6,811,532 B2 | 11/2004 | Ogura et al. |
| 6,846,287 B2 | 1/2005 | Bonadio et al. |
| 6,878,110 B2 | 4/2005 | Yang et al. |
| 6,890,295 B2 | 5/2005 | Michels et al. |
| 6,899,673 B2 | 5/2005 | Ogura et al. |
| 6,916,331 B2 | 7/2005 | Mollenauer et al. |
| 6,945,932 B1 | 9/2005 | Caldwell et al. |
| 6,972,026 B1 | 12/2005 | Caldwell et al. |
| 7,001,397 B2 | 2/2006 | Davison et al. |
| 7,008,377 B2 | 3/2006 | Beane et al. |
| 7,056,321 B2 | 6/2006 | Pagliuca et al. |
| 7,081,089 B2 | 7/2006 | Bonadio et al. |
| 7,195,590 B2 | 3/2007 | Butler et al. |
| 7,214,185 B1 | 5/2007 | Rosney et al. |
| 7,223,257 B2 | 5/2007 | Shubayev et al. |
| 7,223,278 B2 | 5/2007 | Davison et al. |
| 7,235,084 B2 | 6/2007 | Skakook et al. |
| 7,238,154 B2 | 7/2007 | Ewers et al. |
| 7,276,075 B1 | 10/2007 | Callas et al. |
| 7,300,399 B2 | 11/2007 | Bonadio et al. |
| 7,316,699 B2 | 1/2008 | McFarlane |
| 2002/0038077 A1 | 3/2002 | de la Torre et al. |
| 2002/0183594 A1 | 12/2002 | Beane et al. |
| 2003/0014076 A1 | 1/2003 | Mollenauer |
| 2003/0036748 A1 | 2/2003 | Cooper et al. |
| 2003/0114832 A1 | 6/2003 | Kohler et al. |
| 2003/0135091 A1 | 7/2003 | Nakazawa |
| 2003/0208122 A1 | 11/2003 | Melkent |
| 2003/0236549 A1 | 12/2003 | Bonadio et al. |
| 2004/0049099 A1 | 3/2004 | Ewers et al. |
| 2004/0167543 A1 | 8/2004 | Mazzocchi et al. |
| 2004/0230100 A1 | 11/2004 | Shluzas |
| 2005/0215863 A1 | 9/2005 | Ravikumar et al. |
| 2005/0225582 A1 | 10/2005 | Wenchell |
| 2005/0241647 A1 | 11/2005 | Nguyen et al. |
| 2005/0273133 A1 | 12/2005 | Shluzas et al. |
| 2005/0288558 A1 | 12/2005 | Ewers et al. |
| 2006/0020241 A1 | 1/2006 | Piskun et al. |
| 2006/0041188 A1 | 2/2006 | Dirusso et al. |
| 2006/0041232 A1 | 2/2006 | Stearns et al. |
| 2006/0149306 A1 | 7/2006 | Hart et al. |
| 2006/0241651 A1 | 10/2006 | Wilk |
| 2006/0247498 A1 | 11/2006 | Bonadio et al. |
| 2007/0203398 A1 | 8/2007 | Bonadio et al. |
| 2007/0208312 A1* | 9/2007 | Norton et al. ............... 604/284 |
| 2007/0270654 A1 | 11/2007 | Pignato et al. |
| 2007/0276430 A1 | 11/2007 | Lee et al. |
| 2008/0027476 A1 | 1/2008 | Piskun |
| 2008/0103366 A1 | 5/2008 | Banchieri et al. |
| 2008/0200767 A1 | 8/2008 | Ewers et al. |
| 2008/0255519 A1 | 10/2008 | Piskun et al. |
| 2009/0012477 A1 | 1/2009 | Norton et al. |

FOREIGN PATENT DOCUMENTS

| | | |
|---|---|---|
| EP | 1312318 | 5/2003 |
| EP | 1637086 | 3/2006 |
| EP | 1870043 | 12/2007 |

(56) References Cited

FOREIGN PATENT DOCUMENTS

| | | |
|---|---|---|
| EP | 2044889 | 4/2009 |
| WO | 93/14801 | 8/1993 |
| WO | 94/04067 | 3/1994 |
| WO | 97/42889 | 11/1997 |
| WO | 99/16368 | 4/1999 |
| WO | 02/07611 | 1/2002 |
| WO | 2006/100658 | 9/2006 |
| WO | 2006/113216 | 10/2006 |
| WO | 2008/015566 | 2/2008 |
| WO | 2008/121294 | 10/2008 |

OTHER PUBLICATIONS

International Search Report of PCT/US08/03991 dated Jul. 30, 2008. (1 pages).

European Search Report of EP 09252160 dated Mar. 17, 2010 (2 pages).

European Search Report for EP 09252168 dated Mar. 19, 2010 (3 pages).

* cited by examiner

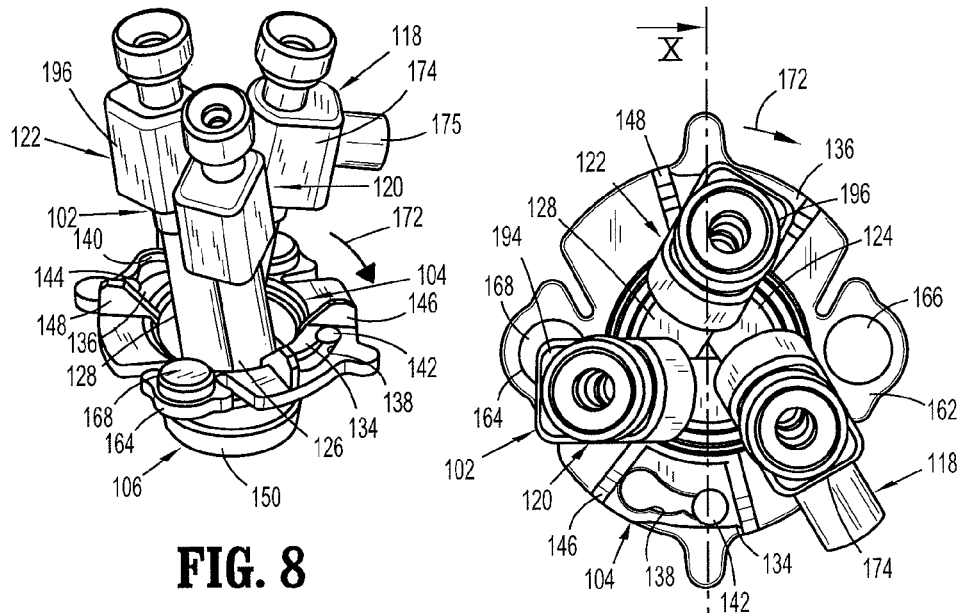
FIG. 8
FIG. 9
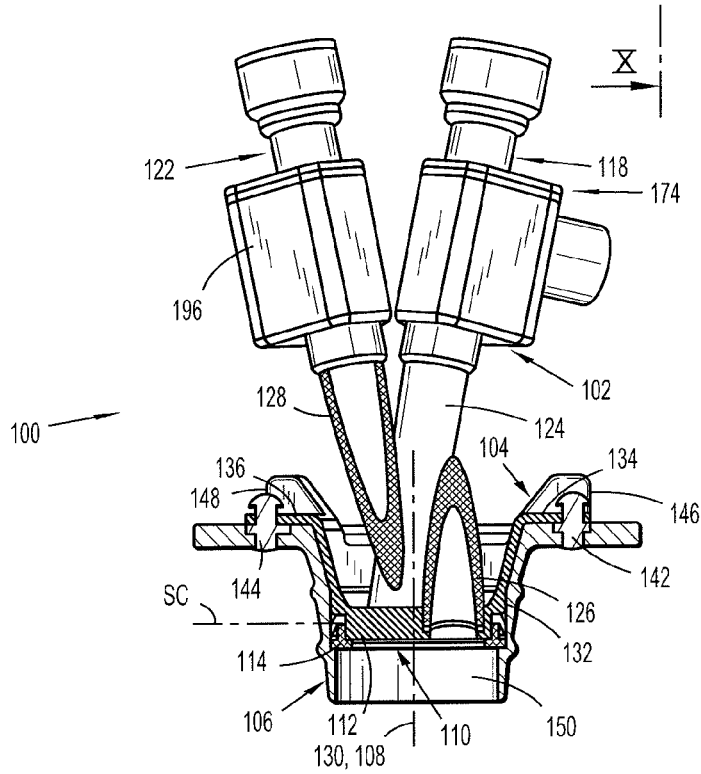
FIG. 10

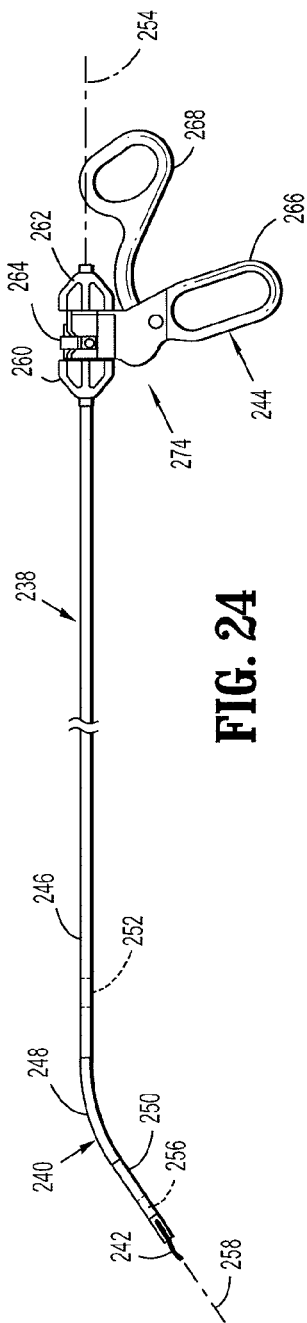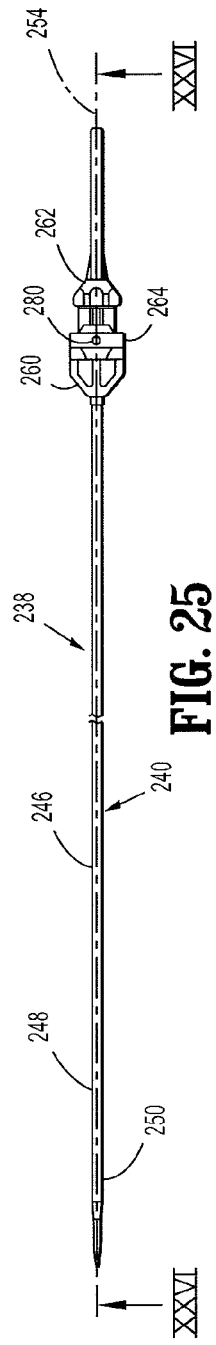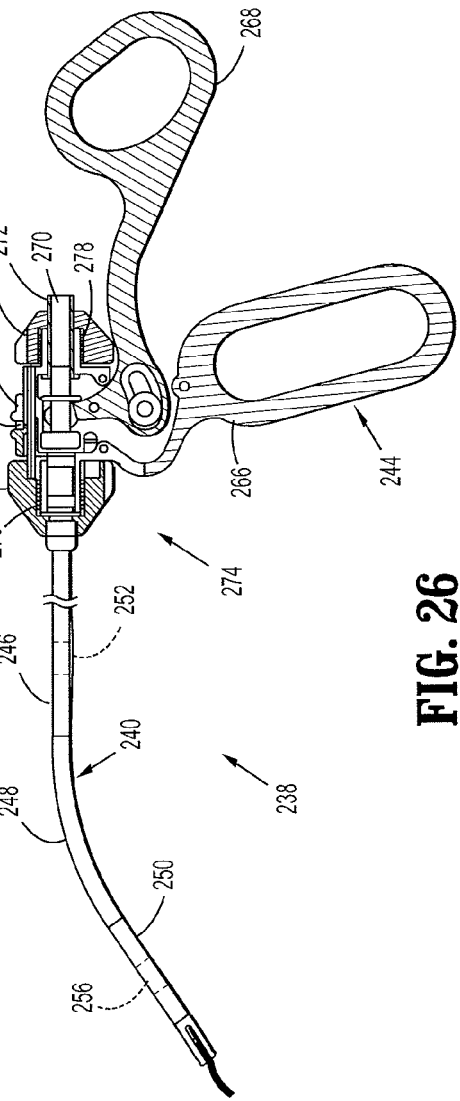

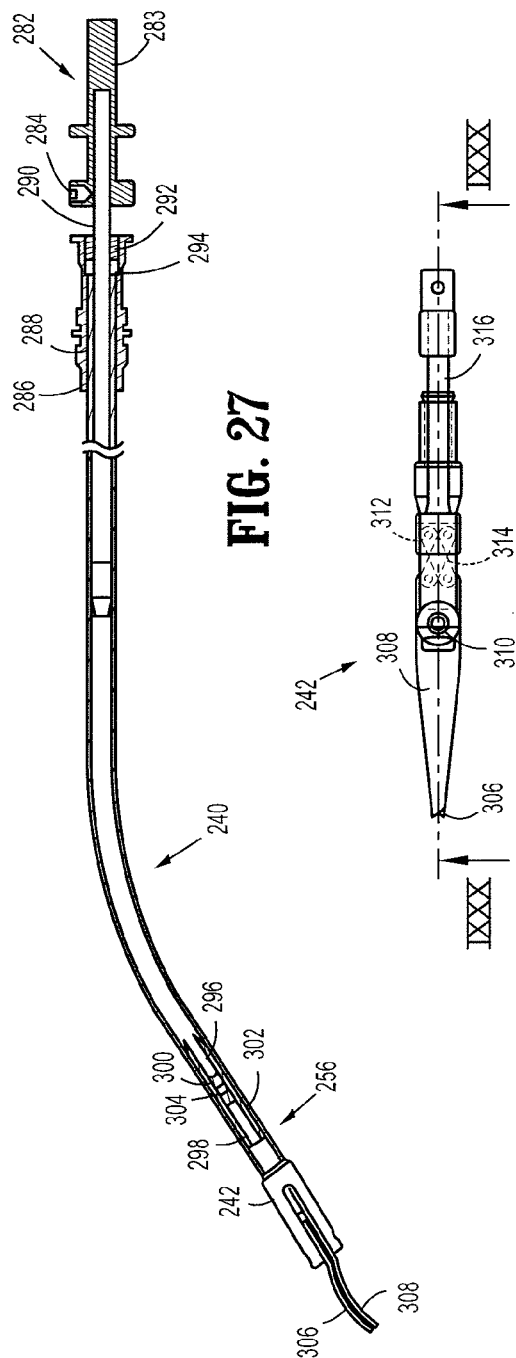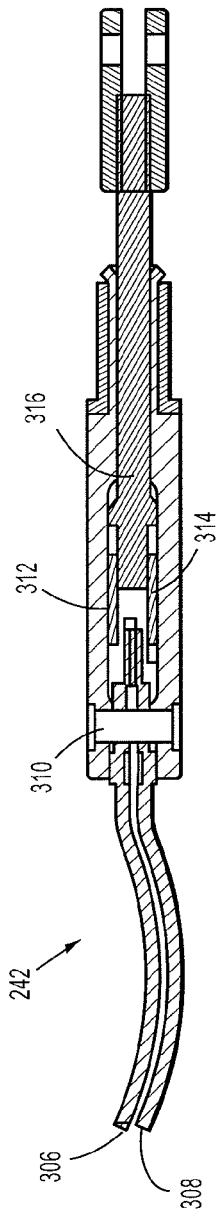

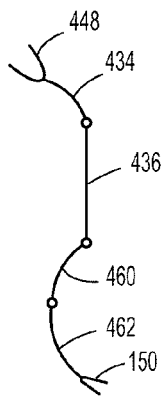 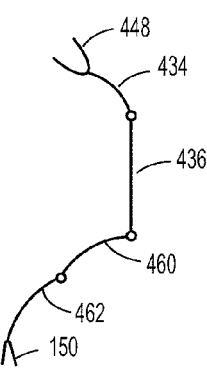 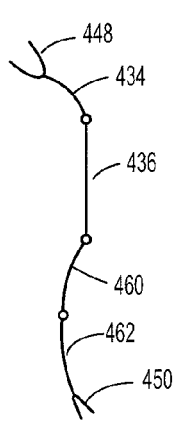 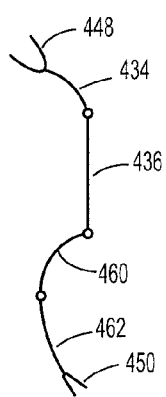
FIG. 32A    FIG. 32D    FIG. 32E    FIG. 32F
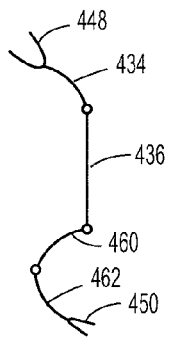
FIG. 32B
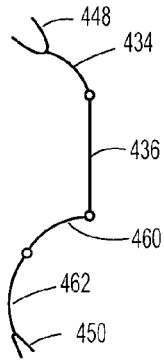
FIG. 32C
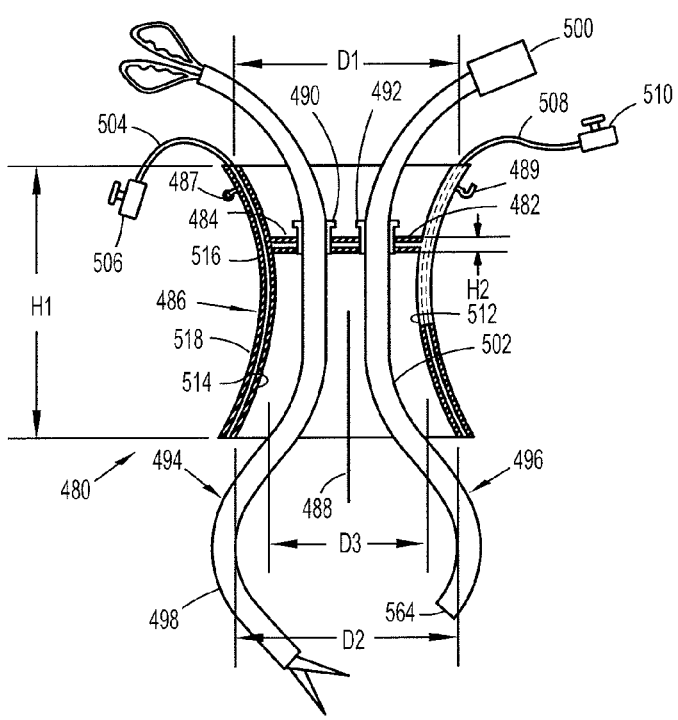
FIG. 33

LAPAROSCOPIC INSTRUMENT AND RELATED SURGICAL METHOD

CROSS REFERENCE TO RELATED APPLICATIONS

The present application claims the benefit of and priority to each one of U.S. Provisional Application Ser. No. 61/191,733 filed on Sep. 11, 2008, and also is a continuation-in-part of U.S. application Ser. No. 10/895,546, filed Jul. 21, 2004 now U.S. Pat. No. 7,753,901 and also is a continuation-in-part of U.S. application Ser. No. 10/668,542, filed Sep. 23, 2003 now U.S. Pat. No. 7,850,600. The entire contents of each of these applications is incorporated herein by reference.

FIELD OF THE INVENTION

The present invention relates to surgical instruments, surgical port assemblies, and an associated method. The instruments, port assemblies and method are particularly useful in the performance of laparoscopic procedures entirely through a single entry path into a patient, for instance, through the umbilicus.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through (one of) the trocar sleeve(s). Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedure. In addition, smaller, 2-3 mm, incisions may still cause undesirable cosmetic outcomes and wound complications (bleeding, infection, pain, keloid formation, etc.).

Since the benefits of smaller and fewer body cavity incisions are proven, it would be attractive to perform an operation utilizing only a single incision in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems, which allow laparoscopic procedures to be performed entirely through the umbilicus while at the same time reducing or eliminating the "chopstick effect". A laparoscopic procedure performed entirely through the umbilicus, using the laparoscopic instruments and trocar system according to an embodiment of the present invention, allows one to accomplish the necessary diagnostic and therapeutic tasks while further minimizing abdominal wall trauma and improving cosmesis.

SUMMARY OF THE INVENTION

The present invention contemplates the facilitation of laparoscopic or minimally invasive surgical procedures wherein several laparoscopic or minimally invasive instruments are inserted into a patient through respective cannulas all extending through the same opening in the patient, for instance, through the umbilicus. The advantages of such an operation include minimizing trauma to the patient and accelerating the patient recovery.

The present disclosure provides instruments and cannula or port assemblies for the performance of surgical procedures, particularly including laparoscopic procedures, for instance, entirely through the umbilicus. The present invention aims in part to provide improved laparoscopic instruments and associated methods for facilitating operations through the umbilicus. The instruments of the present invention can also be used for performance of surgical procedures through single incisions other than through the umbilicus. In addition to laparoscopic procedures, the instruments can be used for thoracoscopic procedures or other endoscopic or minimally invasive procedures.

A medical instrument insertable through a cannula comprises, in accordance with the present invention, an elongate shaft and an operative tip having a first jaw and a second jaw movable with respect to the first jaw, the operative tip disposed distally of a distal end of the distal shaft, the operative tip being disposed for rotation relative to at least a distal end portion of the shaft about a longitudinal axis of the distal end portion.

Pursuant to further features of the present invention, the shaft may include a tubular sheath and the instrument may further comprise a cable or rod member extending longitudinally through the sheath, the cable or rod member being operatively connected to the operative tip for actuating the operative tip and for rotating the operative tip about the axis of the distal end portion. Where the instrument further comprises a handle, the tubular sheath is preferably connected to the handle and rotatable relative to the handle about a longitudinal axis of a proximal portion of the shaft. The cable or rod member is preferably longitudinally shiftable and rotatable relative to the sheath.

Where the operative tip includes a pair of jaws pivotably hinged to one another, the cable or rod member is preferably linked to the jaws for pivoting the jaws. The jaws may be mounted between prongs or legs of a clevis, the clevis being rotatably attached to a distal end of the sheath.

The handle can include a rotary actuator knob operatively linked to the sheath carrying a pair of annular toothed members spring loaded into toothed engagement to provide the rotary knob and the sheath with a plurality of angular rest positions.

The handle may additionally include a ratchet member releasably locking the operative tip in a plurality of different operative configurations. Where the handle includes two first finger grips or handle parts pivotably coupled to one another, the ratchet member is preferably pivotably mounted to one of the finger grips or handle parts and provided with teeth cooperating with a stop on the other of the finger grips or handle parts. The handle may also include a trigger cooperating with the ratchet member for releasing the ratchet member from each of a plurality of locked positions each corresponding to a respective one of the operative configurations of the operative tip. A movable member provided on the handle may cooperate with the ratchet member for deactivating the ratchet member.

The shaft may include a distal end portion extending at an acute angle relative to the proximal shaft portion wherein the proximal shaft portion is rotatable relative to a handle about a longitudinal axis of the proximal shaft portion.

A medical instrument insertable through a cannula comprises, in accordance with another aspect of the present invention, a handle and an elongate shaft having at least two portions including a proximal shaft portion and a distal shaft portion, the proximal shaft portion being attached at a proximal end at least indirectly to the handle, the proximal shaft portion being rotatable relative to the handle about an axis of the proximal shaft portion, the distal shaft portion extending at an angle relative to an axis of the proximal shaft portion. An operative tip is rotatable relative to the distal shaft portion.

A surgical method comprises, in accordance with another aspect of the present invention, (a) inserting a distal end portion of a surgical instrument into a patient, the instrument having a tubular shaft member and first and second jaws, (b) rotating the tubular shaft member about a proximal axis of the tubular shaft member, (c) independently rotating the jaws of the instrument about a distal axis of the tubular shaft member and relative to a distal end of the tubular shaft member, and d) moving at least a first jaw with respect to a second jaw between closed and opened positions.

Where a cable or rod member longitudinally traverses the tubular shaft member, the rotating of the operative tip preferably includes rotating the cable or rod member inside the tubular shaft member.

Where the cable or rod member is operatively connected to the operative tip, the method preferably further comprises longitudinally shifting the cable or rod member relative to the tubular shaft member to move a component of the operative tip about an additional axis oriented at a non-zero angle relative to the distal axis.

Where the distal axis and the proximal axis are oriented at a non-zero angle relative to one another, the rotating of the tubular shaft member preferably entails moving the operative tip along a circular arc about the proximal axis.

A laparoscopic medical instrument insertable through a laparoscopic trocar sleeve comprises, in accordance with another aspect of the present invention, (i) a handle, (ii) an elongate shaft, at least a portion of the shaft being rotatable relative to the handle about a longitudinal axis of the shaft, (iii) an operative tip disposed at a distal end of the distal shaft portion, and (iv) a rotary actuator knob operatively linked to the shaft, the handle carrying a pair of annular toothed members spring loaded into toothed engagement to provide the rotary knob and the shaft with a plurality of angular rest positions. The instrument may include a tubular sheath, in which case the instrument may further comprise a cable or rod member extending longitudinally through the sheath and being operatively connected to the operative tip for actuating the operative tip and for rotating the operative tip about the axis of the distal shaft portion.

The present invention also provides a method of performing a surgical procedure through an incision in a patient comprising the steps of:

inserting a first curved instrument through a first cannula of a cannula assembly, the first instrument having a handle, a shaft and first and second jaws, the jaws being rotatable relative to the shaft and the shaft being rotatable relative to the handle;

inserting a second curved instrument through a second cannula of the cannula assembly, the second instrument having a handle, a shaft and third and fourth jaws, the jaws being rotatable relative to the shaft and the shaft being rotatable relative to the handle; and manipulating the instruments in a crossed configuration.

The method preferably further includes the step of opening and closed the first and second jaws. The method may further include the step of locking the jaws in an open position.

The present invention also provides a surgical access system comprising a cannula assembly, a first curved instrument and a second curved instrument. The cannula assembly includes a first cannula and a second cannula, the first cannula being movable with respect to the second cannula. The first curved instrument has a handle, a shaft and first and second jaws, the jaws being rotatable relative to the shaft and the shaft being rotatable relative to the handle. The second curved instrument has a handle, a shaft and third and fourth jaws, the jaws being rotatable relative to the shaft and the shaft being rotatable relative to the handle.

Preferably, the first instrument includes a jaw actuating mechanism to move the jaws between open and closed positions and the second instrument includes a jaw actuating mechanism to move the jaws between open and closed positions. One embodiment of a surgical port assembly that facilitates the performance of laparoscopic surgical procedures utilizing the above-described instruments and methods may comprise a cannula assembly including at least one cannula member, and a holder disposable in an opening in a patient's skin for receiving the cannula component so that the cannula component is movable relative to the holder during a surgical procedure. Preferably, the cannula unit is rotatable with respect to the holder about a longitudinal axis of the holder or cannula unit. It is contemplated that the holder is fastened to the patient during the surgical operation, so that the cannula unit is movable relative to the patient.

The one cannula may be wholly or partially flexible. The cannula may have a relaxed configuration that is linear.

The cannula unit may be partially insertable into the holder, while the port assembly further comprises a connector member for removably attaching the cannula unit to the holder, the connector also being partially insertable into the holder.

In using laparoscopic instruments pursuant to the present invention, one forms an opening in a patient, inserts a port assembly at least partially through the opening, and inserts a plurality of elongate medical instruments through respective cannulas of the port assembly. During a laparoscopic procedure, the instrument shafts are rotated about respective longitudinal axes and the operative tips of the instruments are rotated relative to the distal ends of the instrument shafts, about longitudinal distal axes of the instrument shafts.

The shafts and in particular the tubular sheath members of the present laparoscopic instruments are substantially rigid throughout so that they cannot be bent. The instrument shafts exemplarily have a hockey-stick shape. Two laparoscopic surgical instruments each having a hockey stick shape are advantageously used in a crossed configuration, which markedly improves the degrees of freedom of the instruments, particularly during lateral (medial-lateral) movements.

Examples of other surgical port assemblies that can be used with the medical instruments described herein are disclosed in patent application Ser. No. 12/079,599, filed Mar. 27, 2008, the entire contents of which is incorporated herein by reference.

BRIEF DESCRIPTION OF THE DRAWINGS

FIG. 8 is a perspective view of the laparoscopic port or cannula assembly of FIGS. 1-3, together with the port holder of FIGS. 4-7, showing the laparoscopic port or cannula assembly inserted into and attached to the port holder.

FIG. 9 is a top plan view of the laparoscopic port or cannula assembly of FIGS. 1-3 connected to the port holder of FIGS. 4-7, as shown in FIG. 8.

FIG. 10 is a longitudinal cross-sectional view taken along line X-X in FIG. 9.

FIG. 24 is a side elevational view of a laparoscopic instrument utilizable with the multiple-cannula port assembly of FIGS. 8-10, in accordance with the present invention.

FIG. 25 is a top plan view of the laparoscopic instrument of FIG. 24.

FIG. 26 is partially a side elevational view and partially a cross-sectional view taken along line XXVI-XXVI in FIG. 25.

FIG. 27 is a partial longitudinal cross-sectional view also taken along line XXVI-XXVI in FIG. 25.

FIG. 28 is a top plan view, on a larger scale, of a distal end of the laparoscopic instrument of FIGS. 24-27.

FIG. 29 is a longitudinal cross-sectional view, on an even larger scale, of the distal end portion shown in FIG. 28.

FIGS. 32A-32F are diagrams of the instrument of FIG. 31, showing different possible operational configurations of the instrument.

FIG. 33 is a schematic cross-sectional view of a laparoscopic instrument or cannula holder with instruments passing therethrough.

DETAILED DESCRIPTION OF THE PREFERRED EMBODIMENTS

Figure 1:
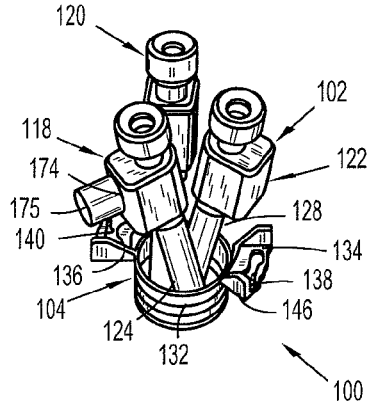
FIG. 1 is a perspective view of a laparoscopic port having multiple cannulas, in accordance with one embodiment of the present invention.
Figure 2:
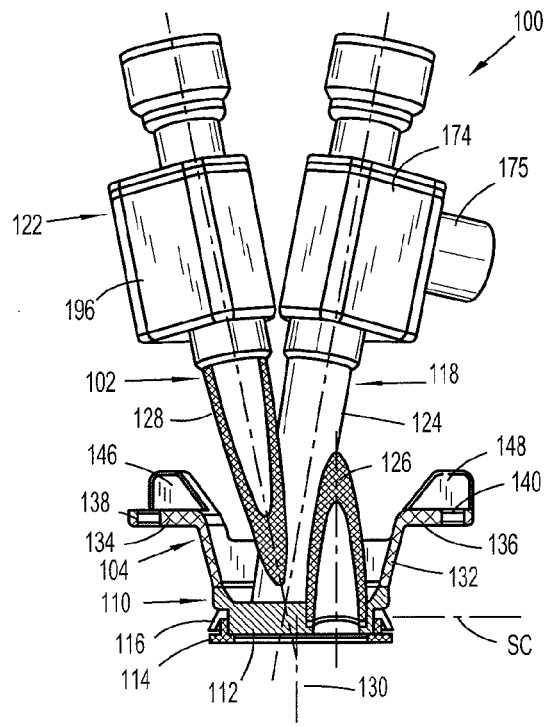
FIG. 2 is a cross-sectional view of the laparoscopic port or cannula assembly of FIG. 1, taken along line II-II in FIG. 3.
Figure 3:
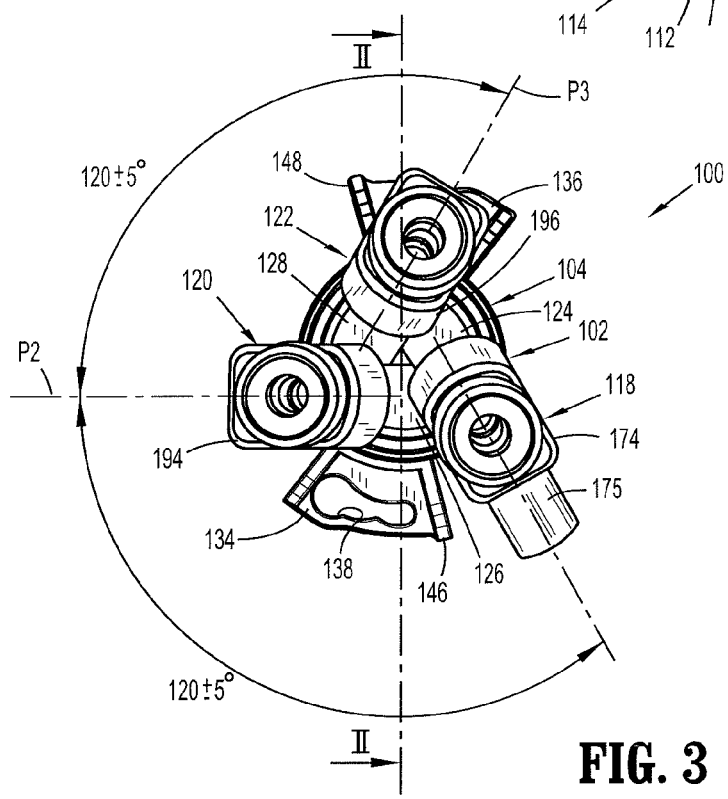
FIG. 3 is a top view of the laparoscopic port or cannula assembly of FIG. 1.
Figure 4:
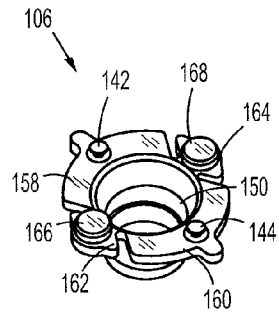
FIG. 4 is a perspective view of an annular holder disposable in an opening in a patient for receiving the laparoscopic port or cannula assembly of FIGS. 1-3.
Figure 5:
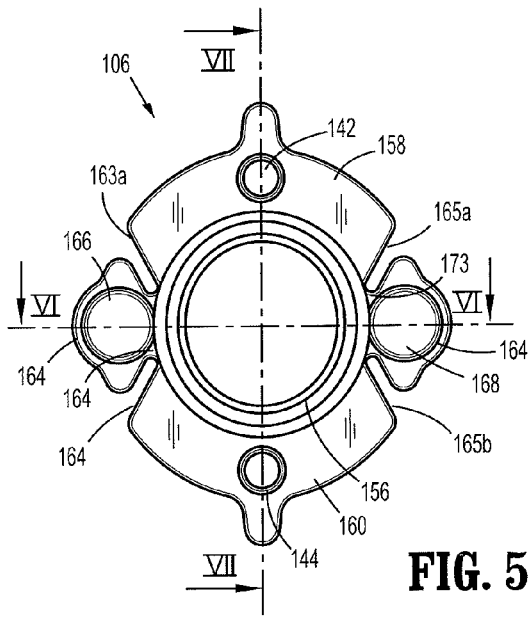
FIG. 5 is a top plan view of the port holder of FIG. 4.
Figure 6:
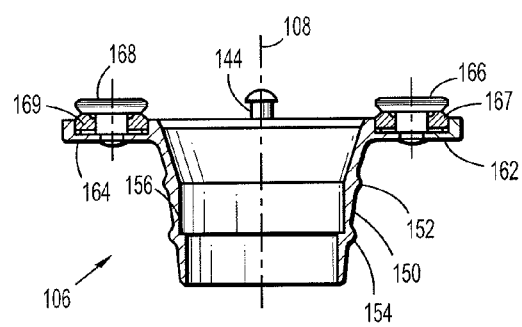
FIG. 6 is a longitudinal cross-sectional view of the port holder of FIGS. 4 and 5, taken along line VI-VI in FIG. 5.
Figure 7:
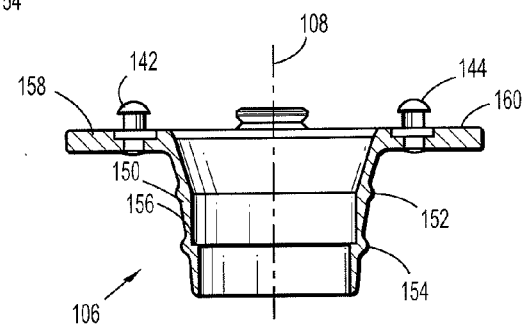
FIG. 7 is another longitudinal cross-sectional view of the port holder of FIGS. 4 and 5, taken along line VII-VII in FIG. 5.
Figure 11:
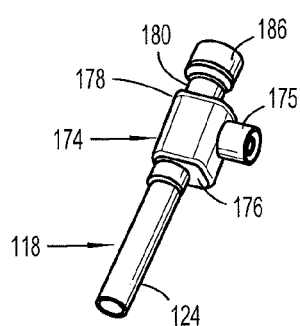
FIG. 11 is a perspective view of a cannula with an insufflation valve, included in the laparoscopic port or cannula assembly of FIGS. 1-3 and 8-10.
Figure 12:
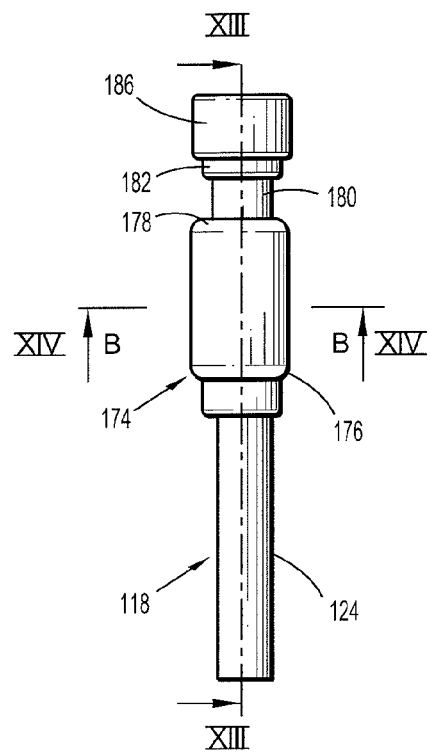
FIG. 12 is a side elevational view of the cannula of FIG. 11, on a larger scale.
Figure 13:
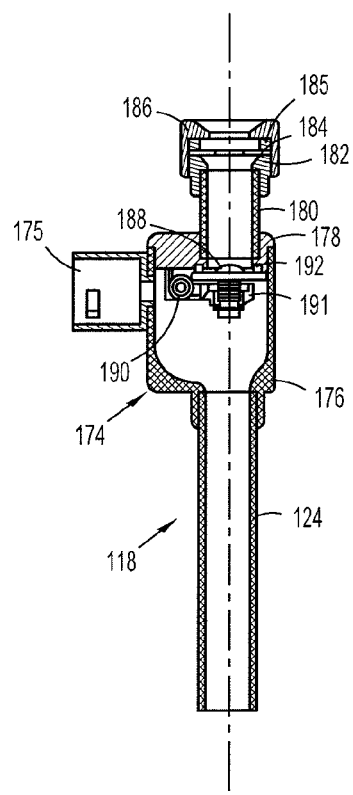
FIG. 13 is a longitudinal cross-sectional view of the cannula of FIGS. 11 and 12, taken along line XIII-XIII in FIG. 12.
Figure 14:
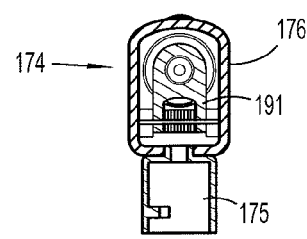
FIG. 14 is a transverse cross-sectional view of the cannula of FIGS. 11 and 12, taken along line XIV-XIV in FIG. 12.
Figure 15:
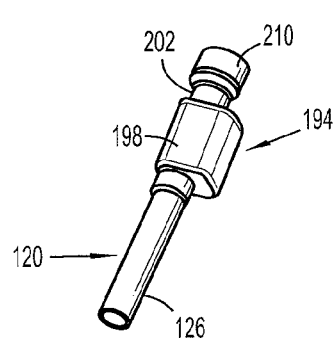
FIG. 15 is a perspective view of a cannula without an insufflation valve, included in the laparoscopic port or cannula assembly of FIGS. 1-3 and 8-10.
Figure 16:
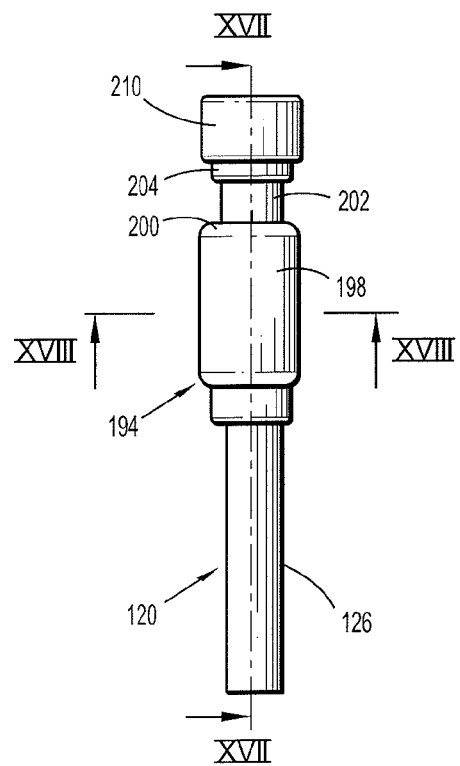
FIG. 16 is a side elevational view of the cannula of FIG. 16, on a larger scale.

As depicted in FIGS. 1-3, a laparoscopic port or cannula assembly 100 comprises a cannula unit 102 and a connector 104 associated therewith for removably fastening the cannula unit to an annular port holder 106 (FIGS. 4-8 and 10) that is disposed in an opening (e.g., formed in the umbilicus) in a patient. Cannula unit 102 is coupled to port holder 106 by connector 104 so as to permit rotation of cannula unit 102 about a longitudinal axis 108 (FIGS. 7 and 10) of holder 106.

Cannula unit 102 comprises a base or frame 110 that is insertable into and removably attachable to port holder 106. Base or frame 110 includes a planar panel or wall 112 defining a closure surface or plane SC extending, during a laparoscopic surgical procedure, substantially tangentially to the patient's skin at the opening through with port holder 106 extends. Base or frame 110 further includes a seating ring 114 and a sealing ring 116.

Cannula unit 102 additionally comprises three cannula members 118, 120, 122 each connected to base or frame 110 and defining a respective access path through closure surface SC. Cannula members 118, 120, 122 each extend at an acute angle relative to closure surface SC so that the cannulas are inclined relative to the patient's skin surface during a laparoscopic surgical procedure. Cannula members 118, 120, 122 include flexible tubular portions 124, 126, 128 that have linear configurations in a relaxed or unstressed condition.

Each cannula member 118, 120, 122 defines a respective plane P1, P2, P3 (FIG. 3) oriented perpendicularly to closure surface or plane CS (the main plane) and spaced from a longitudinal axis 130 of base or frame 110. These secondary planes P1, P2, and P3 are disposed at angles of 120° relative to each other, as indicated in FIG. 3. Connector 104 is loosely coupled to cannula unit 102 so as to be freely movable along axis 130 of the cannula unit, between base 110 and valve components of cannulas 118, 120, 122.

Connector 104 includes a frustoconical portion 132 insertable into port holder 106 (see FIG. 10) and further includes a pair of flanges 134, 136 for temporarily locking cannula unit 102 to holder 106. To that end, flanges 134, 136 are provided with dual-lobed slots 138, 140 for receiving respective pins or projections 142, 144 on port holder 106 (see FIGS. 4, 5, 7, 8, 9). Flanges 134 and 136 are also provided with respective pairs of upturned ears 146 and 148 functioning in part as thumb and finger rests for swiveling connector 104 about axis 108 (and 130) to reversibly secure connector 106 and concomitantly cannula unit 102 to port holder 106.

As illustrated in FIGS. 4-7, port holder 106 includes a tapered, slightly frustoconical sleeve 150 provided along an outer surface with a pair of annular beads or ribs 152 and 154 and along an inner surface with a shoulder 156 that serves as an abutment or rest for seating ring 114 of cannula unit 102. At a wider end of sleeve 150, holder 106 includes a pair of diametrically opposed flanges 158, 160 and a pair of diametrically opposed ears 162, 164. Pins or projections 142, 144 are rigid with flanges 158, 160, while ears 162, 164 carry respective flat-headed posts 166, 168 around which sutures are wound to fasten holder 106 to the skin of the patient. Rubber gaskets 167 and 169 may be provided for clamping suture threads to posts 166 and 168. Alternatively or additionally, sutures anchoring port holder 106 to the body wall of the patient may be inserted through slots 163a, 163b and 165a, 165b and partially wrapped around bases 171 and 173 of ears 162, 164 (see FIG. 5).

After placement of holder 106 in an opening in the patient (and after removal of an insert assist member 170, FIGS. 19-22, from the holder), base or frame 110 of cannula unit 102 is inserted into holder 106 until seating ring 114 engages shoulder 15 (see FIG. 10). Cannula unit 110 is secured to holder 106 by an insertion and a subsequent rotation of connector 104 relative to holder 106, as indicated by an arrow 172 in FIGS. 8 and 9, so that projections 142, 144 and slots 138, 140 are interlocked (see FIGS. 8-10). After this locking of connector 104 to holder 106, cannula unit 102 is rotatable about axes 108 and 130 in opposition to a frictional drag force exerted by virtue of sealing ring 116.

As illustrated in FIGS. 11-14, cannula unit 118 includes valve component 174 connected to tubular portion 124. Valve component 124 includes an insufflation port 175 for receiving a tube (not shown) for guiding carbon dioxide gas from a pressurized source into the patient. As shown particularly in FIG. 13, valve component 124 of cannula member 118 includes a valve box or casing 176 with a cover or closure 178 to which an extension tube 180 is attached. At an end opposite valve casing 176, extension tube 180 is provided with a sleeve 182, a valve seal 184, a disc 185, and a cap 186. Valve component 174 further includes a valve door 188 that is biased into a closure position shown in FIG. 13 by a helical or coil spring 190. Door 188 is supported by a mounting bracket and associated hardware 191. An O-ring seal 192 is provided for inhibiting the escape of insufflation gas from a patient through extension tube 124 when a laparoscopic surgical instrument does not traverse cannula member 118.

Figure 17:
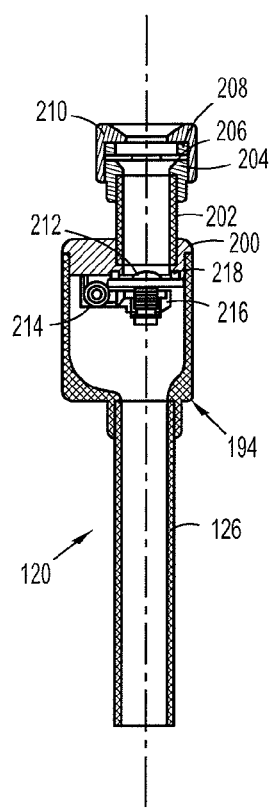
FIG. 17 is a longitudinal cross-sectional view of the cannula of FIGS. 15 and 16, taken along line XVII-XVII in FIG. 16.
Figure 18:
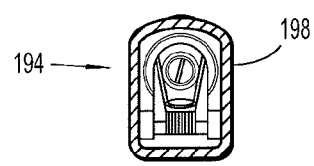
FIG. 18 is a transverse cross-sectional view of the cannula of FIGS. 15 and 16, taken along line XVIII-XVIII in FIG. 16.

As illustrated in FIGS. 1-3 and 8-10, cannula members 120 and 122 include respective valve components 194 and 196 connected to respective flexible tubular portions 126 and 128. These valve components are structurally identical, a representative component 194 being depicted in FIGS. 15-18. Valve component 194 includes a valve box or casing 198 with a cover or closure 200 to which an extension tube 202 is attached. At an end opposite valve casing 198, extension tube 202 is provided with a sleeve 204, a valve seal 206, a disc 208, and a cap 210. Valve component 194 further includes a valve door 212 that is biased into a closure position shown in FIG. 17 by a helical or coil spring 214. Door 212 is supported by a mounting bracket and associated hardware 216. An O-ring seal 218 is provided for inhibiting the escape of insufflation gas from a patient through extension tube 202 when a laparoscopic surgical instrument does not traverse the respective cannula member 120 (or 122).

Figure 19:
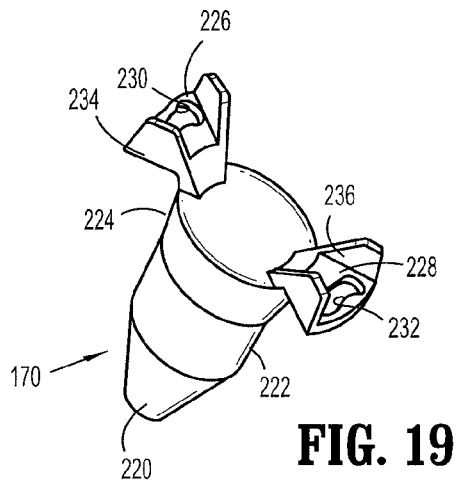
FIG. 19 is a perspective view of an insertion plug used to facilitate insertion of the port holder of FIGS. 4-7 in a patient at the beginning of a laparoscopic procedure.
Figure 20:
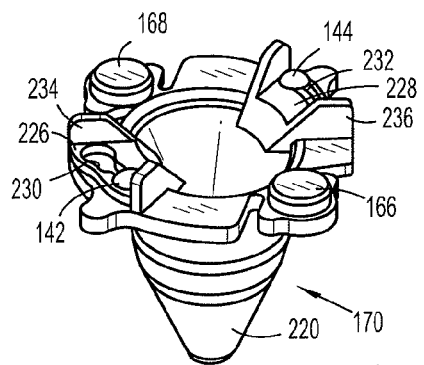
FIG. 20 is a top perspective view of the insertion plug of FIG. 19 temporarily inserted in and attached to the port holder of FIGS. 4-7.
Figure 21:
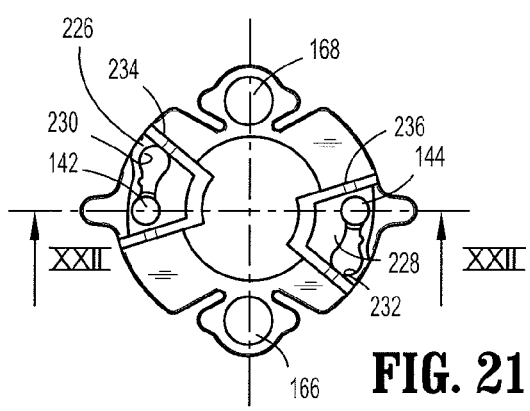
FIG. 21 is a top plan view of the assembled insertion plug and port holder of FIG. 20.
Figure 22:
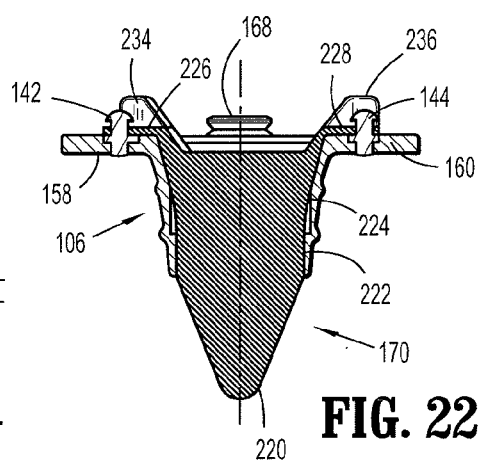
FIG. 22 is a longitudinal cross-section taken along line XXII-XXII in FIG. 21.
Figure 23:
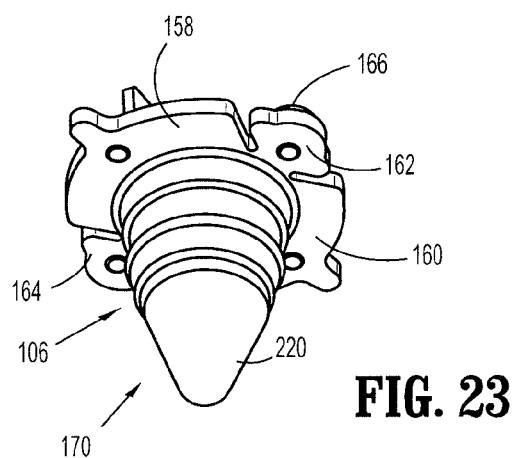
FIG. 23 is a bottom perspective view of the assembled insertion plug and port holder of FIGS. 20-22.

As shown in FIG. 19, insert assist member 170 includes a rounded conical tip 220, a cylindrical middle portion 222 and a slightly tapered or frustoconical outer portion 224. Outer portion 224 is provided with a pair of flanges 226, 228 for temporarily locking insert assist member 170 to port holder 106. To that end, flanges 226, 228 are provided with dual-lobed slots 230, 232 for receiving respective pins or projections 142, 144 on port holder 106, as depicted in FIGS. 20-22. Flanges 226 and 228 are formed with respective pairs of upturned ears 234 and 236 that are manually engageable by a user to reversibly secure connector insert assist member 170 to port holder 106.

After a small incision or opening is made in a patient, port holder 106 with insert assist member 170 connected thereto is inserted through the incision. Sutures (not shown) are stitched to the patient and are wound around and tied to posts 166, 168 to firmly secure the port holder 106 to the patient. Insert assist member 170 is then removed, by a reverse rotation unlocking flanges 226, 228 from pins or projections 142, 144 and by separating the inset assist member from holder 106. Cannula unit 102 is then attached to holder 106 as described above.

FIGS. 24-29 depict a laparoscopic surgical instrument 238 insertable through a laparoscopic trocar sleeve or cannula such as cannula member 118, 120, or 122 of the port assembly of FIGS. 1-3 and 8-10 for executing a laparoscopic surgical operation. It should also be appreciated that the laparoscopic instrument 238 as well as other instruments described herein are insertable through other cannulas, such as the cannulas disclosed in commonly assigned co-pending patent application Ser. No. 12/079,599, filed Mar. 27, 2008. The entire contents of this application is incorporated herein by reference. Instrument 238 comprises an elongate shaft 240, an operative tip 242 disposed at one end of the shaft, and a hand-grip-type actuator 244 disposed at an opposite end of the shaft. Actuator 244 is operatively connected to operative tip 242 via shaft 240 for controlling the operation of the operative tip.

Shaft 240 has a straight proximal end portion 246, a curved middle portion 248 and a straight distal end portion 250, the distal end portion extending at a non-zero angle with respect to the proximal end portion, as shown in FIGS. 24, 26 and 27. Proximal end portion 246 is provided with a first rotary joint 252 so that distal end portion 250 and operative tip 242 are rotatable about a longitudinal axis 254 of proximal end portion 246. Distal end portion 250 is provided with a second rotary joint 256 so that operative tip 242 is rotatable about a longitudinal axis 258 of the distal end portion. A rotary actuator or knob 260 disposed at the proximal end of instrument 238 is operatively connected to proximal end portion 246 of instrument 240 for rotating distal end portion 250 and operative tip 242 about longitudinal axis 254. Another rotary actuator or knob 262 disposed at the proximal end of instrument 238 is operatively connected to distal end portion 250 of shaft 240 for rotating operative tip 242 about longitudinal axis 258.

Proximal end portion 246, middle portion 248 and distal end portion 250 of instrument shaft 240 are each substantially rigid throughout and can only be rotated about joints 252 and 256 and not bent. The angle between axes 254 and 258 are such that shaft 240 has a shape reminiscent of a hockey stick. In an alternative embodiment of instrument 238, middle portion 248 of shaft 240 may be flexible to permit shaft 240 to alternately assume a linear configuration and the hockey-stick configuration of FIGS. 24 and 26. In that case, a handle assembly 274 is provided with an actuator (not shown) for enabling a bending of middle portion 248.

As shown in FIGS. 24-26, instrument 238 may be provided with further actuators, such as a slidable toggle switch 264, for example for performing a locking function or inducing a pivoting of operative tip 242 about an axis perpendicular to axis 258.

Actuator 244 includes a hand grip member 266 fixed relative to shaft 240 and further includes a pivotable hand grip 268. A proximal end 270 of shaft 240 is journaled in a bearing 272 about which rotary knob 262. Actuator 244, rotary knobs 260 and 262, and toggle switch 264 are parts of a handle assembly 274 also incorporating yokes 276 and 278, a stopper pin 278, a set screw 280.

FIG. 27 illustrates further parts of a shaft assembly 282 including shaft 240, a slider member 283, a socket set screw 284, an outer bearing 286, a motion bar 288, a bend tube 290, a ring 292, and an O-ring seal 294.

Rotary joint 256 is representative of joint 254 and comprises, as shown in FIG. 27, a proximal pin or inner shaft portion 296, a distal pin or inner shaft portion 298, a pair of coupling elements 300 and 302, and a transverse connector pin 304.

As illustrated in FIGS. 28 and 29, operative tip 242 exemplarily includes a pair of jaws 306 and 308 pivotably connected to a distal end of distal end portion 250 via a pivot pin 310. Jaws 306 and 308 are rotatable about pin 310 through the action of levers or arms 312, 314 that pivot in response to a longitudinal motion of a tip rod 316.

After a deployment of cannula unit 102 in a patient as described above, operative tip 242 and shaft 240 of instrument 238 are insertable for example through a cannula member 118, 120, or 122, with the respective tubular portion 124, 126, or 128 bending to accommodate the bent shaft 240. The bent shape of shaft 240, as well as the rotary joints 252 and 256 facilitate the performance of laparoscopic surgical procedure using multiple laparoscopic instruments extending through a single opening in a patient, for instance, in the umbilicus. Such a procedure involves the rotation of distal end portion 250 and operative tip 242 together about axis 254 and the rotation of operative tip about axis 258. In addition, the entire instrument assembly including cannula unit 102 and multiple instruments 238 can be rotated about collinear axes 108 and 130, to optimize the simultaneous or successive access of multiple operative tips 242 to a surgical site inside a patient.

As can be appreciated, when two laparascopic instruments 238 are inserted through the cannula members of FIGS. 1-3, they are positioned and manipulatable in a crossed configuration. Due to the configuration of the shaft (or in alternate embodiments the ability to change the angle of a portion of the shaft), the instrument tips are angled toward each other and toward the target site to facilitate the surgical procedure.

Figures 30, 31:
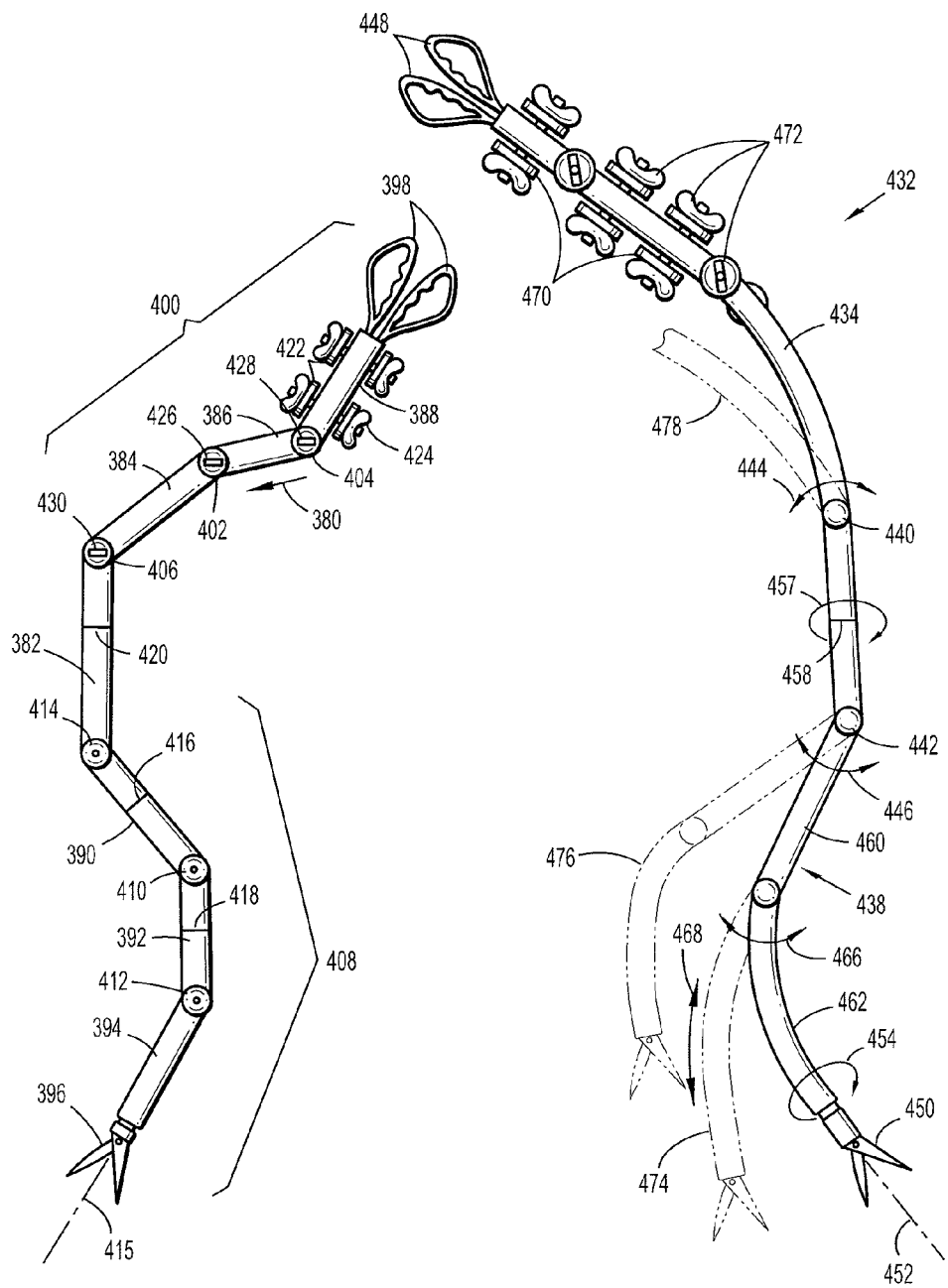
FIG. 30 is a schematic side elevational view of a laparoscopic instrument in accordance with another embodiment of the present invention.
FIG. 31 is a schematic side elevational view of another laparoscopic instrument in accordance with the present invention.

As illustrated in FIG. 30, a stand-alone laparoscopic medical instrument in accordance with an alternate embodiment is insertable through a laparoscopic trocar sleeve or cannula. The instrument comprises an elongate shaft 380 formed of a plurality of a plurality of rigid cylindrical segments including a middle segment 382, three proximal end segments 384, 386, and 388, and three distal end segments 390, 392, and 394. During a laparoscopic procedure utilizing the instrument of FIG. 30, middle segment 382 traverses a laparoscopic cannula, trocar sleeve, or instrument holder as described herein, while proximal end segments 384, 386, and 388 are located outside the patient and distal end segments 390, 392, and 394 are located inside the patient. An operative tip 396 is disposed at one end of the shaft 380, more particularly at a free end of distal end segment 394, and actuator handles or hand grips 398 are disposed at an opposite end of the shaft, more particularly at a free end of proximal end segment 388. Actuator handles 398 are operatively connected to operative tip 396 via shaft 380 for controlling the operation of the tip.

Proximal end segments 384, 386 and 388 form a proximal shaft portion 400 that is independently bendable to form, for example, a C shaped configuration. Proximal end segments 384, 386, and 388 are connected to one another via joints or articulations 402 and 404 and to middle segment 382 via a joint or articulation 406.

Distal end segments 390, 392 and 394 form a distal shaft portion 408 that is independently bendable to form, for example, a C shaped configuration. Distal end segments 390, 392, and 394 are connected to one another via joints or articulations 410 and 412 and to middle segment 382 via a joint or articulation 414.

Operative tip 396 may be rotatable about a longitudinal axis 415. Further rotational capability may be provided by including a joint 416, 418, 420 along distal end segments 390, 392 or middle segment 382, where relative rotation of proximal and distal parts is effectuated about a longitudinal axis of the respective segment.

Proximal end portion 388 is provided with rotary actuators or knobs 422 for modifying the angles between adjacent distal end segments 390, 392, 394, for rotating operative tip 396 relative to distal end segment 394 about axis 414, and for implementing the longitudinal-axis rotation at joints 416, 418, and/or 420. Wing-nut-type clamps 424 may be provided at knobs 422 for releasably locking those actuators to maintain the angles between adjacent distal end segments 390, 392, 394, the rotary position of operative tip 396, and the longitudinal-axis rotation at joints 416, 418, and/or 420.

Clamping elements 426, 428, 430 may be provided at the articulations or joints 402, 404, 406 for locking the relative positions of middle segment 382, and proximal end segments 384, 386, 388. Alternatively, further knobs and wing-nut clamps (not shown) may be provided at the proximal end of the instrument for changing the angles between pairs of adjacent segments 382, 384, 386, 388.

During a laparoscopic surgical procedure, the axial position of operative tip 396 may be adjusted by sliding the laparoscopic instrument of FIG. 30 into and out of the patient, for example, by modifying the position of middle segment 382 relative to the respective cannula or instrument holder aperture. In addition, the axial position of operative tip 396 may be changed by adjusting the configuration of distal end portions 390, 392, 394 relative to one another. Strongly arced configurations have a shorter axial extent than configurations with more shallow arcs. Further degrees of freedom in the positioning of operative tip 396 relative to a surgical site are provided by the rotatability of operative tip 396 about axis 414 and the rotatability at joints 416, 418, 420. The positional adjustability provided by articulations or joints 410, 412, 414 greatly enhances the practical capabilities of the instrument.

FIG. 31 depicts another stand-alone laparoscopic medical instrument having a shaft 432 insertable through a laparoscopic trocar sleeve or cannula. Shaft 432 has a continuously flexible proximal end portion or segment 434, a rigid straight middle portion or segment 436, and a distal end portion 438. Proximal end portion 434 and distal end portion 436 are connected to opposite ends of middle portion 436 via respective articulations or joints 440 and 442, so that the proximal end portion and the distal end portion are laterally swingable relative to the middle portion, as indicated by dual headed arrows 444 and 446. Middle portion 436 constitutes about one-third of the total length of shaft 432.

Shaft 432 is provided at a proximal end, i.e., at the free end of proximal end portion 434, with a pair of hand grip actuators 448, and is further provided at a distal end, i.e., at the free end of distal end portion 438 with an operative tip 450 such as a scissors, a forceps, a clamp, a cauterizing element, etc. Operative tip 450 is rotatable about a longitudinal axis 452 relative to the end of distal end portion 438, as indicated by a bidirectional arrow 454. As indicated by another bidirectional arrow 457, proximal end portion 434 and distal end portion 438 may be rotable relative to one another about a longitudinal instrument axis 456, owing to a rotable joint 458 exemplarily provided along middle portion 436.

Distal end portion 438 includes two segments or sections 460 and 462 pivotably connected to one another via an articulation or joint 464, as indicated by a dual headed arrow 466. Distal-most section 462 is continuously bendable along its length into an infinite number of smoothly curved generally C-shaped configurations, as indicated by an arrow 468. The more proximal section 460 may be rigid and linear or, alternatively, also continuously flexible along substantially its entire length and formable into a multitude of smoothly arced generally C-shaped configurations.

Proximal end portion 434 is provided along a linear proximal section (not separately labeled) with a plurality of actuator knobs 470 and locking elements 472 for controllably modifying (a) the degree of curvature of proximal end portion 434 and distal end portion 438, particularly distal-most section 462, (b) the angles between portions 434 and 436 and portions 436 and 438, (c) the angle between sections 460 and 462, (d) the degree and direction of rotation of operative tip 450 about axis 452, and (e) the relative angular position of proximal end portion 434 and distal end portion 438, as determined by the operational status of joint 458. By way of illustration, a modified position and curvature of distal-most section 462 is indicated in FIG. 31 at 474. A modified position of proximal section 460 and a corresponding modified curvature of distal most section 462 are indicated in phantom at 476. An alternate position of proximal end portion 434 with respect to middle portion 436 is shown in phantom at 478.

FIGS. 32A-32F depict additional possible positional and curvature configurations of the instrument of FIG. 31, particularly distal end portion 438.

During a laparoscopic surgical procedure, the axial position of operative tip 450 may be adjusted by sliding the laparoscopic instrument of FIG. 31 into and out of the patient, for example, by modifying the position of middle portion 436 relative to the respective cannula or instrument holder aperture. In addition, the axial position of operative tip 450 may be changed by adjusting the configuration of distal end portion 438, as depicted in FIGS. 32A-32F. Strongly arced configurations (FIGS. 32B and 32C) have a shorter axial extent than configurations with more shallow arcs (FIGS. 32A, 32E). Further degrees of freedom in the positioning of operative tip 450 relative to a surgical site are provided by the rotatability of operative tip 450 about axis 452 and the rotatability at joint 458.

One or more of the actuator mechanisms including knobs 470 and locking elements 472 may be operatively connected to shaft 432 for bending distal section 462 (and optionally section 460) in a direction out of the plane of the drawing sheet.

Where proximal portion 434 of shaft 432 assumes a first C-shaped configuration in response to operation of a respective one of the knobs 470 and distal portion 438 (or 462) of the shaft assumes a second C-shaped configuration in response to operation of a second one of the knobs 470, the C-shaped configurations may face opposite sides of the shaft, thus forming shaft 432 into a generally S-shape.

Figure 34:
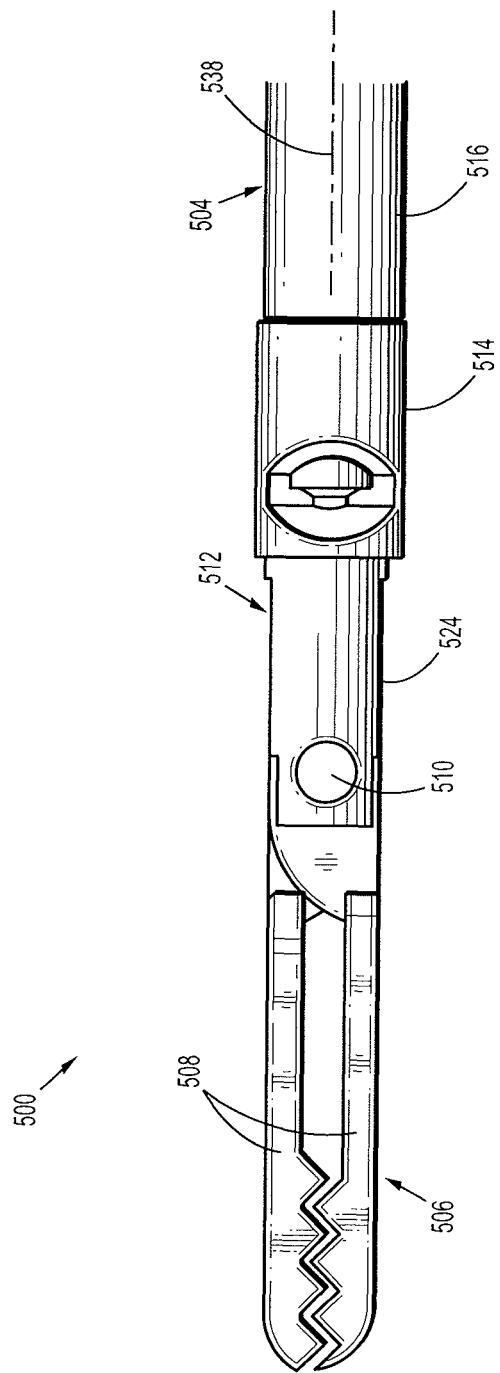
FIG. 34 is a side elevational view of a distal end portion of a laparoscopic instrument in accordance with another alternate embodiment the present invention.
Figure 35:
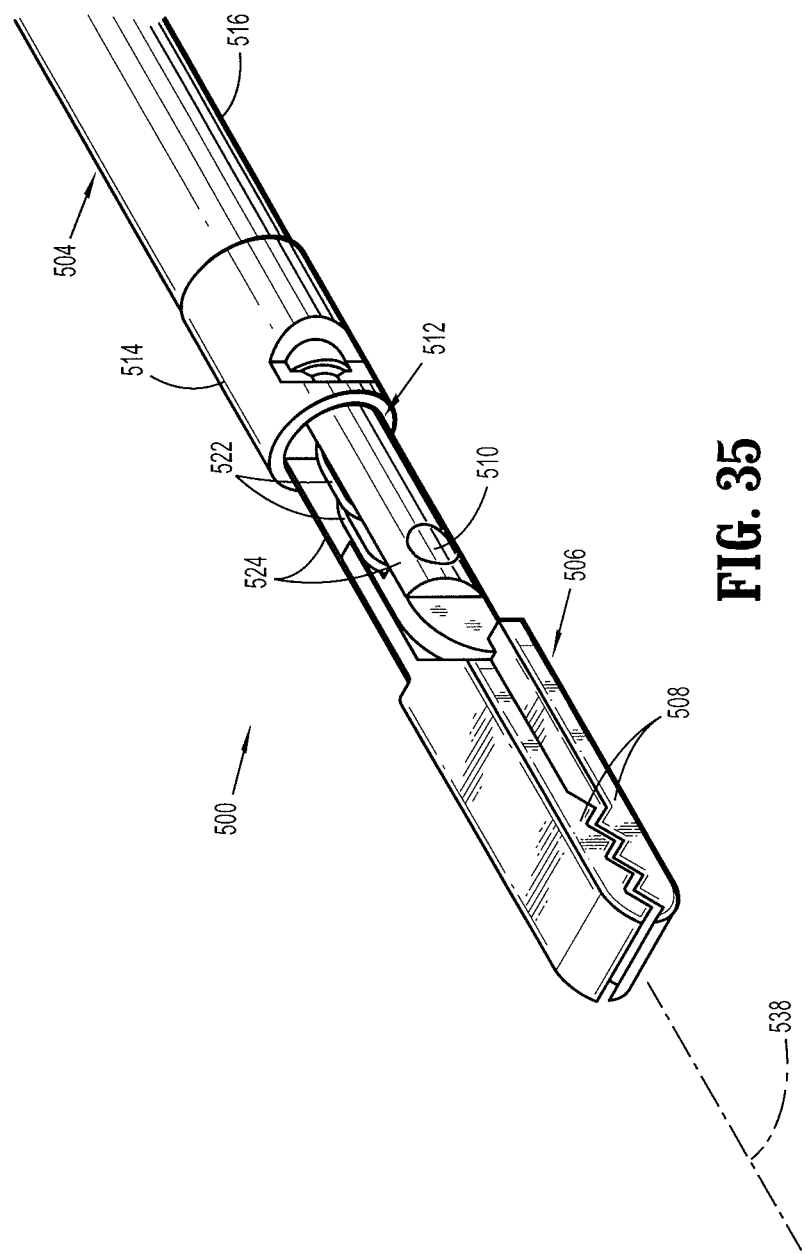
FIG. 35 is a front perspective view of the laparoscopic instrument end portion of FIG. 34.
Figure 36:
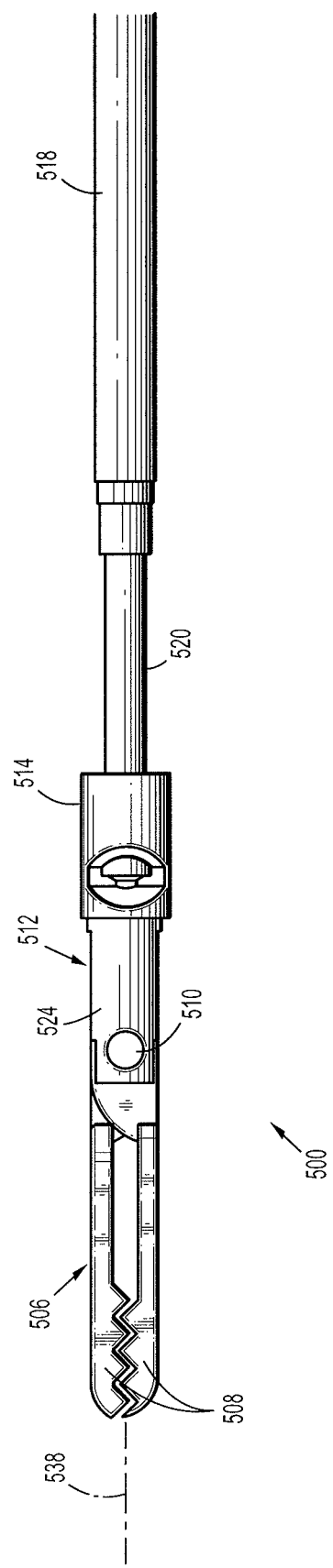
FIG. 36 is a partial side elevational view of the instrument end portion of FIGS. 33 and 34, with a tubular sheath member removed for clarity.
Figure 37:
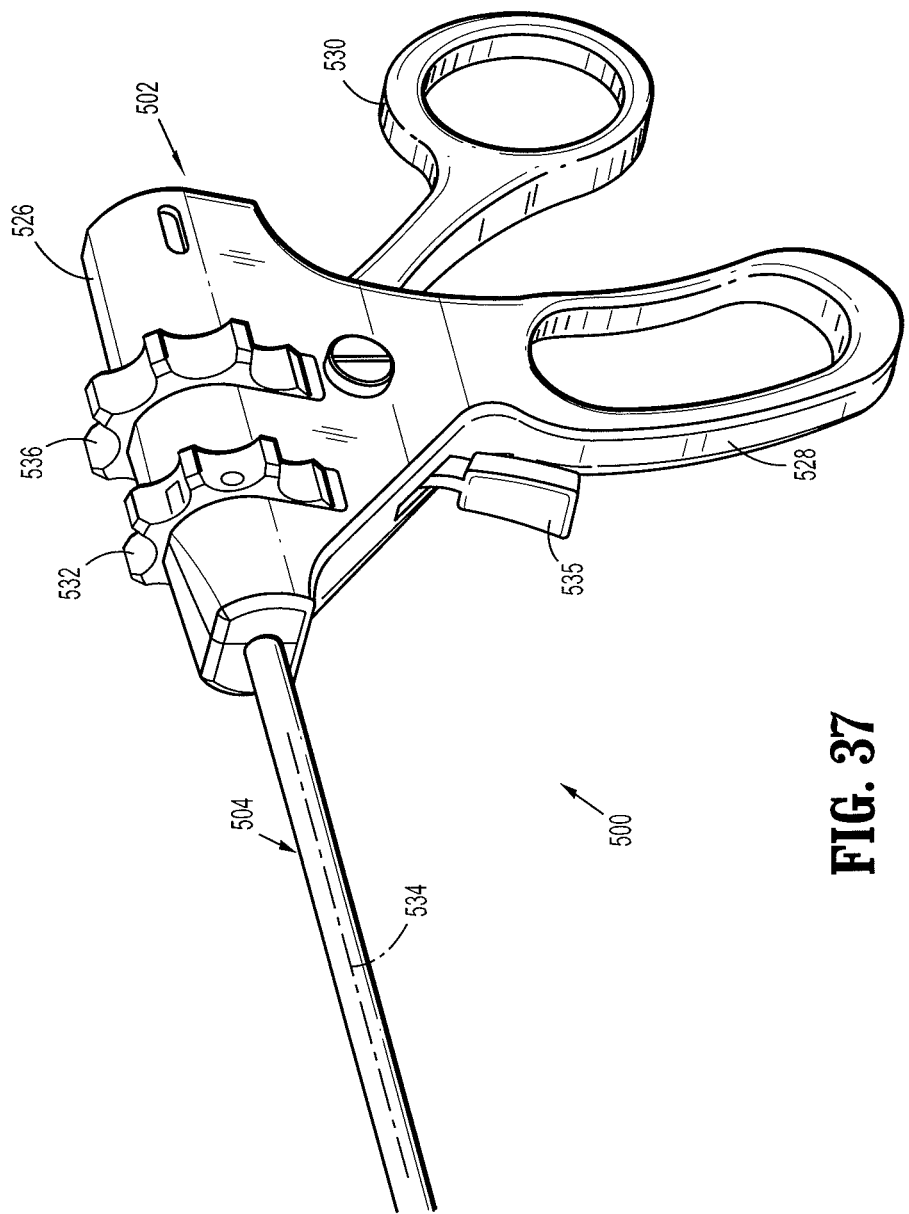
FIG. 37 is a front perspective view of a handle portion of the instrument of FIGS. 34-36.
Figure 38:
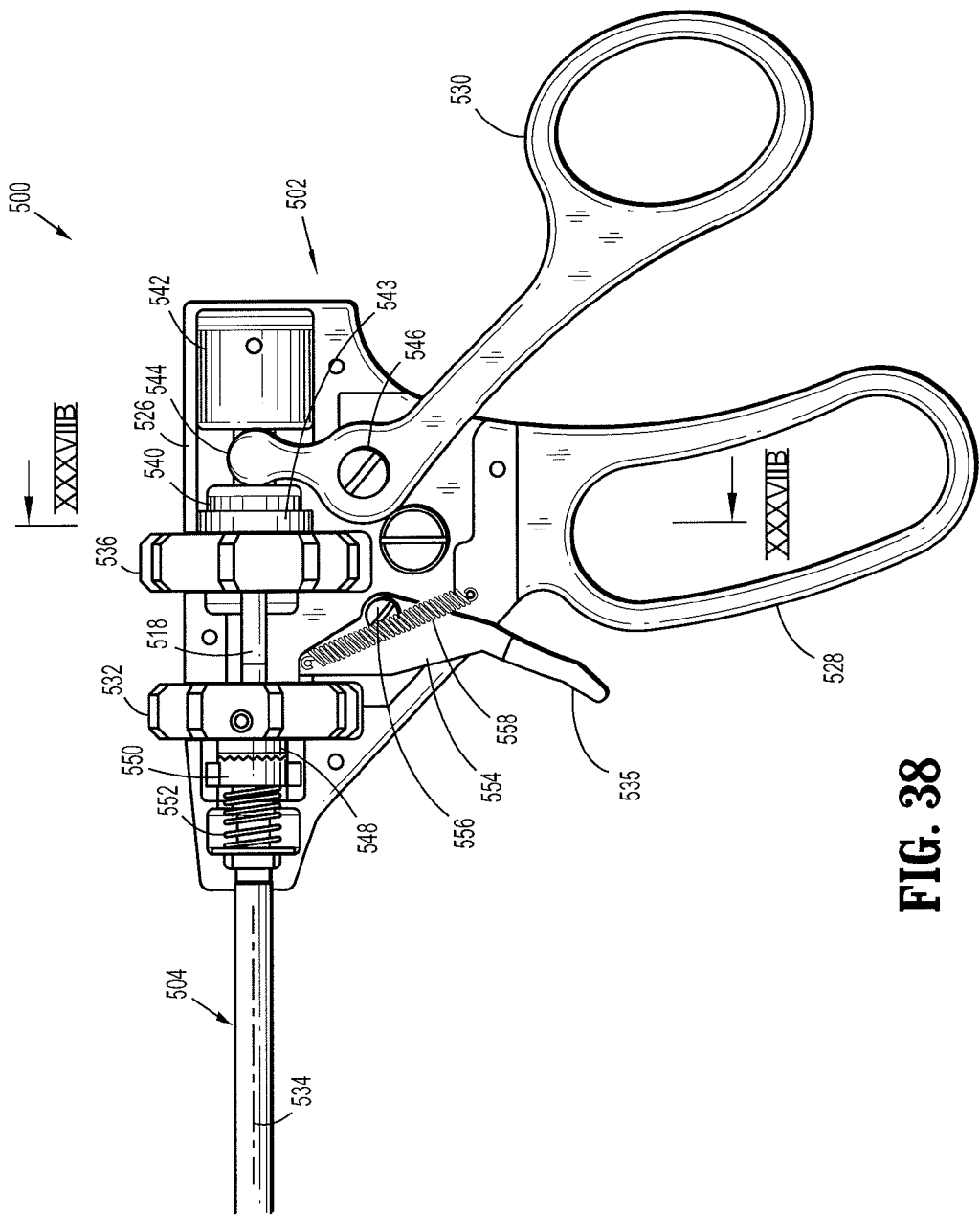
FIG. 38 is a longitudinal cross-sectional view of the handle portion of FIG. 37.

FIGS. 34-36 depict a distal end portion of an alternate embodiment of a laparoscopic instrument, designated by reference numeral 500, while FIGS. 37 and 38 show the handle and actuator assembly 502 at the proximal end of the instrument. The instrument is preferably sterilizable and reusable. As shown in FIGS. 34 and 35, instrument 500 includes a shaft 504 and an operative tip or end effecter 506 operatively connected to and extending from the distal end of the shaft. End effecter 506 exemplarily includes a pair of grasper jaws 508 pivotably connected via a pivot pin 510 to one another and to a rigid clevis member 512. (Although grasper jaws 508 (and 568 described below) are shown by way of example, other types of jaws are contemplated such as other grasper jaw configurations and jaws configured for cutting and severing tissue.) Clevis 512 is in turn rotatably connected and longitudinally fixed to an annular coupling element 514. Thus, clevis 512 is rotatable relative to the coupling element 514 but longitudinally stationary relative thereto. Coupling element 514 is in turn fixed to a distal tip of a tubular sheath member 516 that forms an outer part of shaft 504.

Figure 34A:
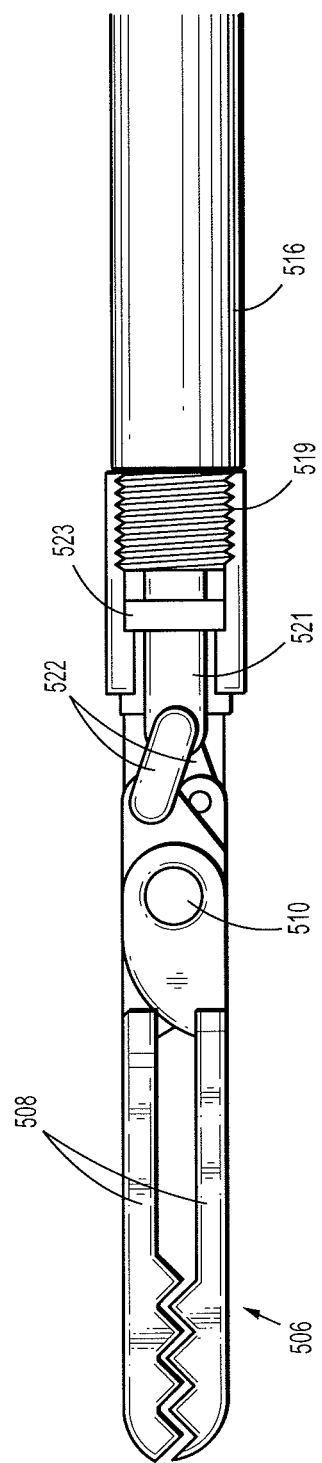
FIG. 34A is a side elevational view similar to FIG. 34 but partially broken away in cross-section.

A flexible cable member 518 is positioned within sheath member 516 (FIGS. 36 and 38) and is connected at a distal end to a rigid rod 520. Rod 520 traverses coupling element 514 and a rear end portion of clevis 512 and pivotally connects via links 522 to rear or proximal ends of jaws 508 in a space (not labeled) between two prongs 524 of clevis 512. As shown in FIG. 34A, sheath member 516 is connected to coupling element 514 via mating screw threads 519, while rod 520 terminates in an elongate tab or plate 521 that pivotably carries links 522 at its distal end. Tab or plate 521 traverses a rectangular slot (not shown) in a support disk 523 that is rotatably seated in coupling element 514.

A longitudinal motion of cable 518 and rod 520 relative to sheath member 516, coupling element 514 and clevis 512 induces jaws 508 to turn about pivot pin 510 to open and closed configurations. Rod 520 is rotatably entrained to clevis 512, for instance, via jaws 508 and pivot pin 510, so that a rotation of cable 518 and rod 520 relative to tubular sheath member 516 and coupling member 514 about a longitudinal axis 538 of the distal end (not separately labeled) of sheath member 516 rotates jaws 508 and clevis 512 relative to coupling element 514 and sheath member 516.

Figure 38A:
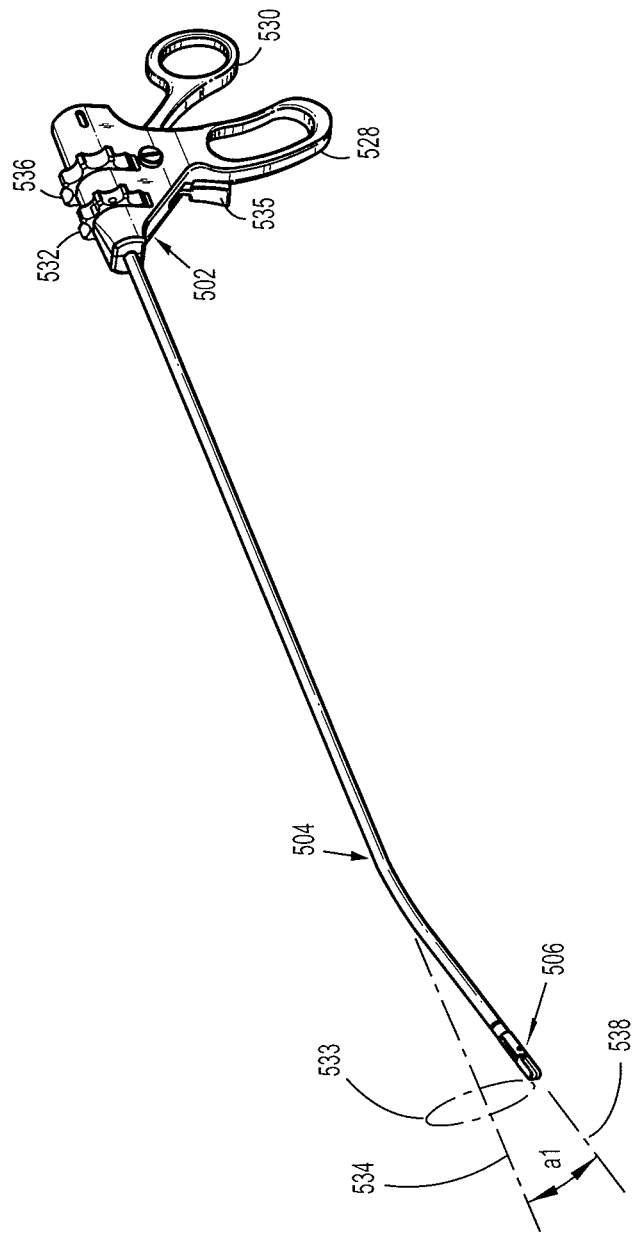
FIG. 38A is a perspective view of the entire instrument of FIGS. 34-38, showing a bend at the distal end of the instrument shaft.

As shown in FIG. 38A, longitudinal axis 538 and the associated distal end portion (FIGS. 34-36) of shaft 504 and sheath member 516 are oriented at an acute angle a1 relative to a longitudinal axis 534 of a proximal portion (FIGS. 37 and 38) of shaft 504 and sheath member 516. Thus, shaft 504 may be angled to form a "hockey-stick" configuration, like that illustrated in FIGS. 24 and 26.

As illustrated in FIGS. 37 and 38, handle and actuator assembly 502 of instrument 500 includes a housing 526, a finger grip 528 stationary relative to the housing, and a thumb grip 530 that is pivotably connected to the housing. A first rotary knob 532 on housing 526 is used for rotating shaft 504 about longitudinal axis 534 of the shaft at the handle and actuator assembly 502. Because of the hockey-stick-type bend depicted in FIG. 38A, a turning of knob 532 moves operative tip or end effecter 506 along a circular arc 533 about axis 534. The angled shaft of the instrument 500 (as well as the other instruments described herein, including instrument 560 described below) results in the instrument tips of two (or more) separate instruments angling toward each other when inserted into the body through cannula members as described herein. The rotational movement of the tips, and the rotational movement of the shaft to move the tips in a circular arc, increase the range of movement of the instrument tip and thus improve accessibility to the target site in the relatively minimal space provided in minimally invasive surgical procedures.

Figure 37A:
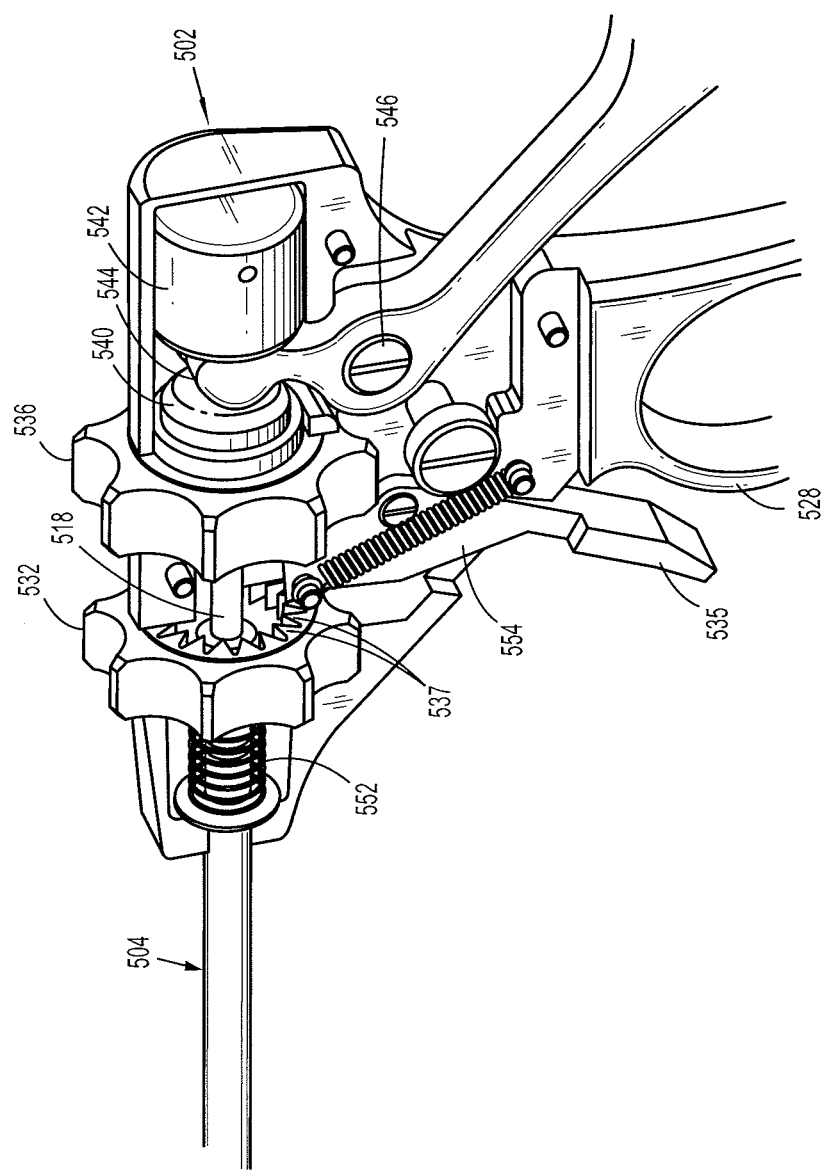
FIG. 37A is a partial rear perspective view, with a housing half-shell removed, of the handle of FIG. 37.

As depicted in FIG. 37A, rotary knob 532 is formed along a rear side with a plurality of inwardly pointing teeth 537. Rotary knob 532 is automatically locked at any desired one of a plurality of angular positions or orientations (18 in the disclosed embodiment), the locking being releasable via a lever or trigger 535 operable by an index finger to maintain a distal end portion of shaft 504.

As further illustrated in FIGS. 37 and 38, handle and actuator assembly 502 includes a second rotary knob 536 for rotating operative tip or end effecter 506 about longitudinal axis 538 of a distal end portion of shaft 504. To that end, rotary knob 536 is rotationally entrained to a proximal end of cable member 518 (see FIG. 38) while cable 518 is longitudinally translatable relative to knob 536. At a proximal end, cable member 518 is fixed to a pair of spaced cylinders 540 and 542 that cooperate with thumb grip or movable handle lever 530 to effectuate the alternate opening and closing of end effector jaws 508. Thumb grip or handle lever 530 carries a ball 544 that is received between cylinders 540 and 542 for enabling a linear shifting of cable member 518 regardless of the angular position of rotary knob 536. Thumb grip or handle lever 530 is swingably secured to handle housing 526 via a pivot pin 546. Thus, the jaws 508 are normally in the closed position. To open the jaws, handle lever 530 is moved toward finger grip 528, thereby pulling cable member 518 proximally as the cylinders 540, 542 are forced in a proximal direction.

Figure 37B:
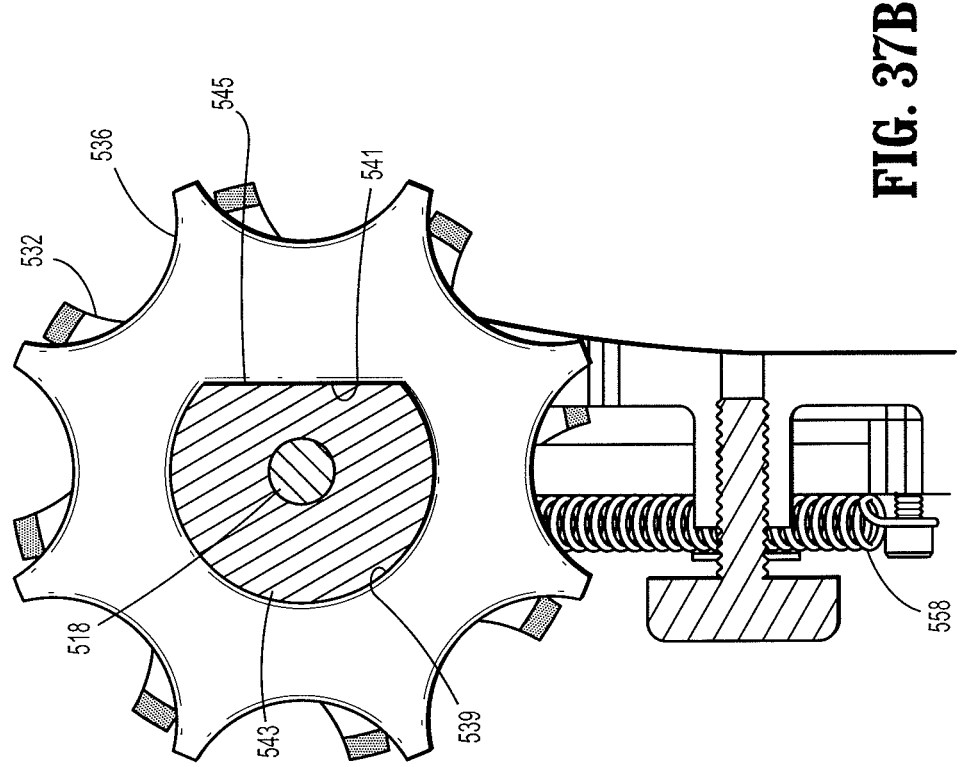
FIG. 37B is a partial cross-sectional view taken along line XXXVIIB-XXXVIIB in FIG. 38.

As depicted in FIG. 37B, knob 536 is formed with a sectioned aperture 539 generally having a D-shape with a straight edge 541. An enlarged portion 543 of cylinder 540 is provided with a flat 545 in a region about knob 536. Flat 545 engages edge 541 and prevents rotation of cable 518 relative to knob 536, while permitting longitudinal sliding of the cable relative to the knob.

Rotary knob 532 carries a unitary toothed hub 548 that meshes with a cylindrical toothed clutch 550 that is slidably but not rotatably mounted to housing 526. Clutch 550 is biased towards hub 548 by a helical spring 552. The spring constant is sufficiently small that turning knob 532 easily pushes clutch member 550 in a distal direction against the biasing force of spring 552 under a camming action between the teeth (not designated) of hub 548 and clutch 550. Clutch member 550 and hub member 548 illustratively have eighteen teeth whereby knob 532 and operative tip or end effector 506 have eighteen discrete angular rest positions about axis 534. A different number of teeth and angular rest positions is also contemplated.

Rotary knob 532 is formed on a rearward or proximal side with eighteen grooves or slots (not separately designated) defined by teeth 537 (FIG. 37A), that alternately receive a leading edge of a locking plate 554 rigid with trigger 535, to temporarily fix or lock rotary knob 532 in a respective one of its eighteen alternative angular positions. A different number of angular positions is also contemplated. Locking plate and release trigger 525 are pivotably mounted to housing 526 via a pivot pin 556 and biased by a helical tension spring 558 into a locking position in engagement with knob 532.

Figure 39:
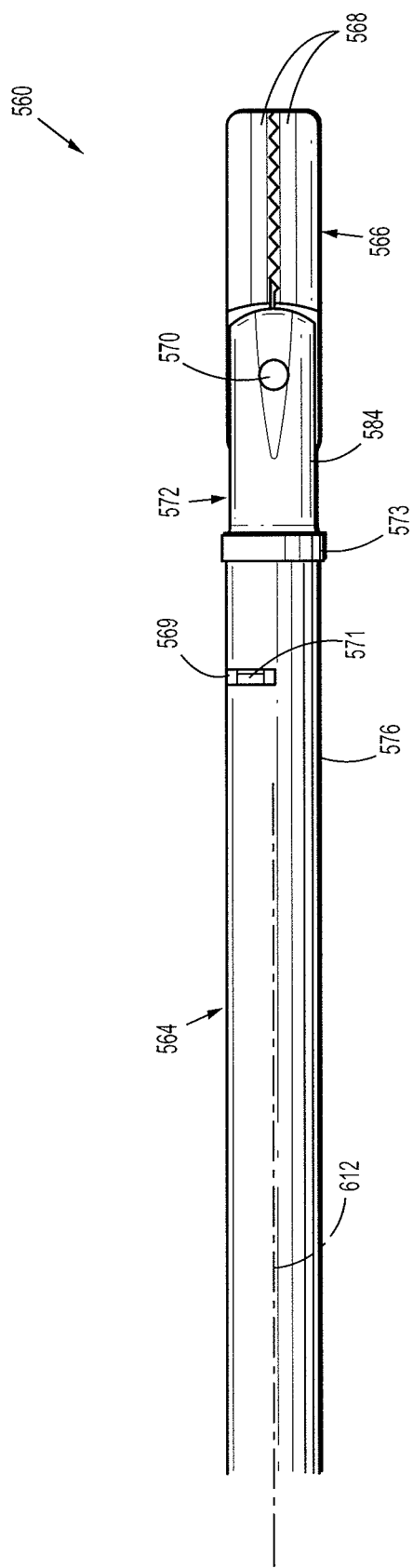
FIG. 39 is a side elevational view of a distal end portion of yet another embodiment of a laparoscopic instrument in accordance with the present invention.
Figure 40:
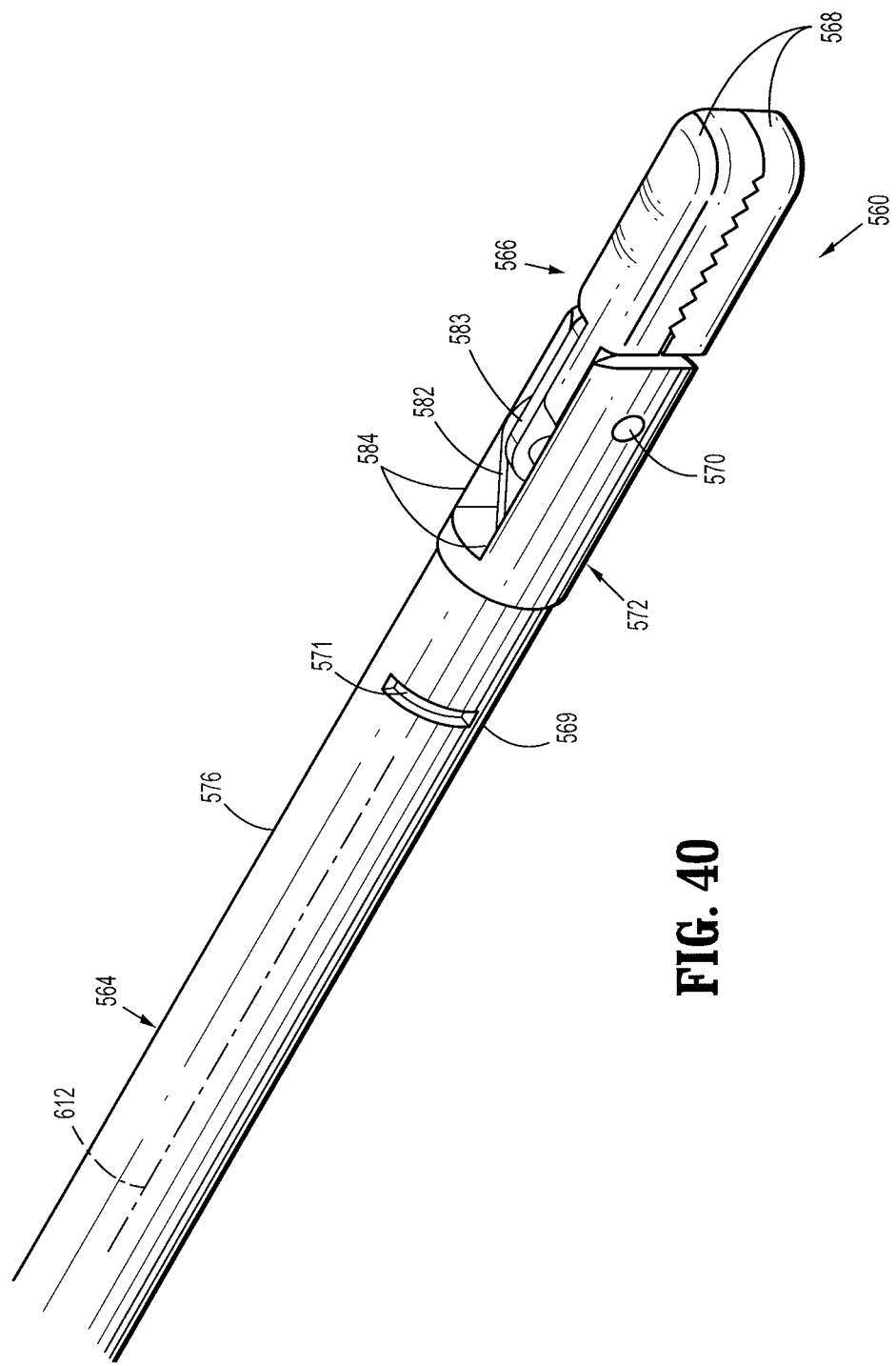
FIG. 40 is a front perspective view of the laparoscopic instrument end portion of FIG. 39.
Figure 41:
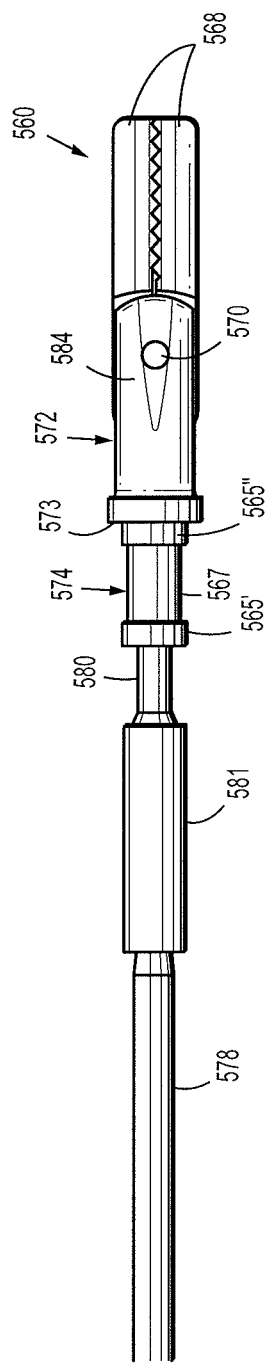
FIG. 41 is a partial side elevational view of the instrument end portion of FIGS. 39 and 40, with a tubular sheath member removed.
Figure 42:
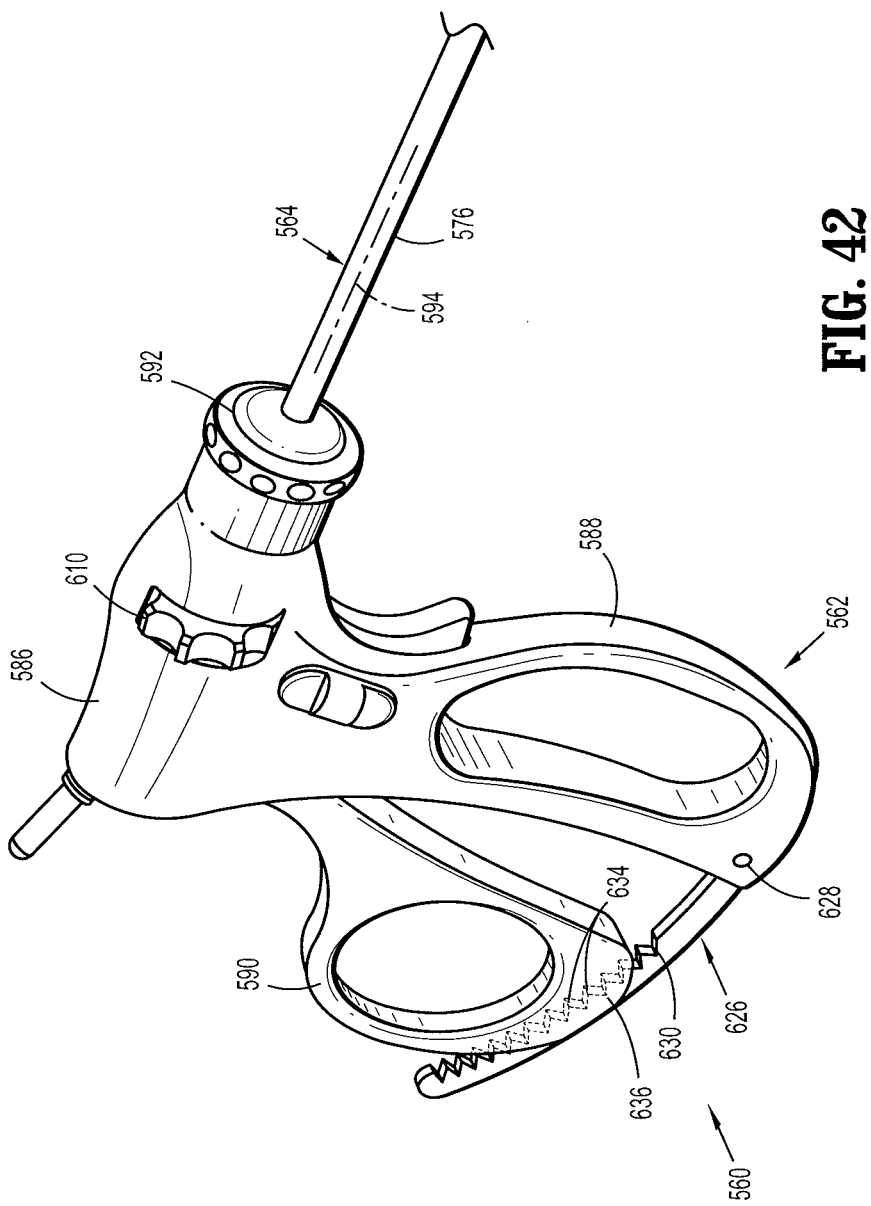
FIG. 42 is a front perspective view of a handle portion of the instrument of FIGS. 39-41.
Figure 43:
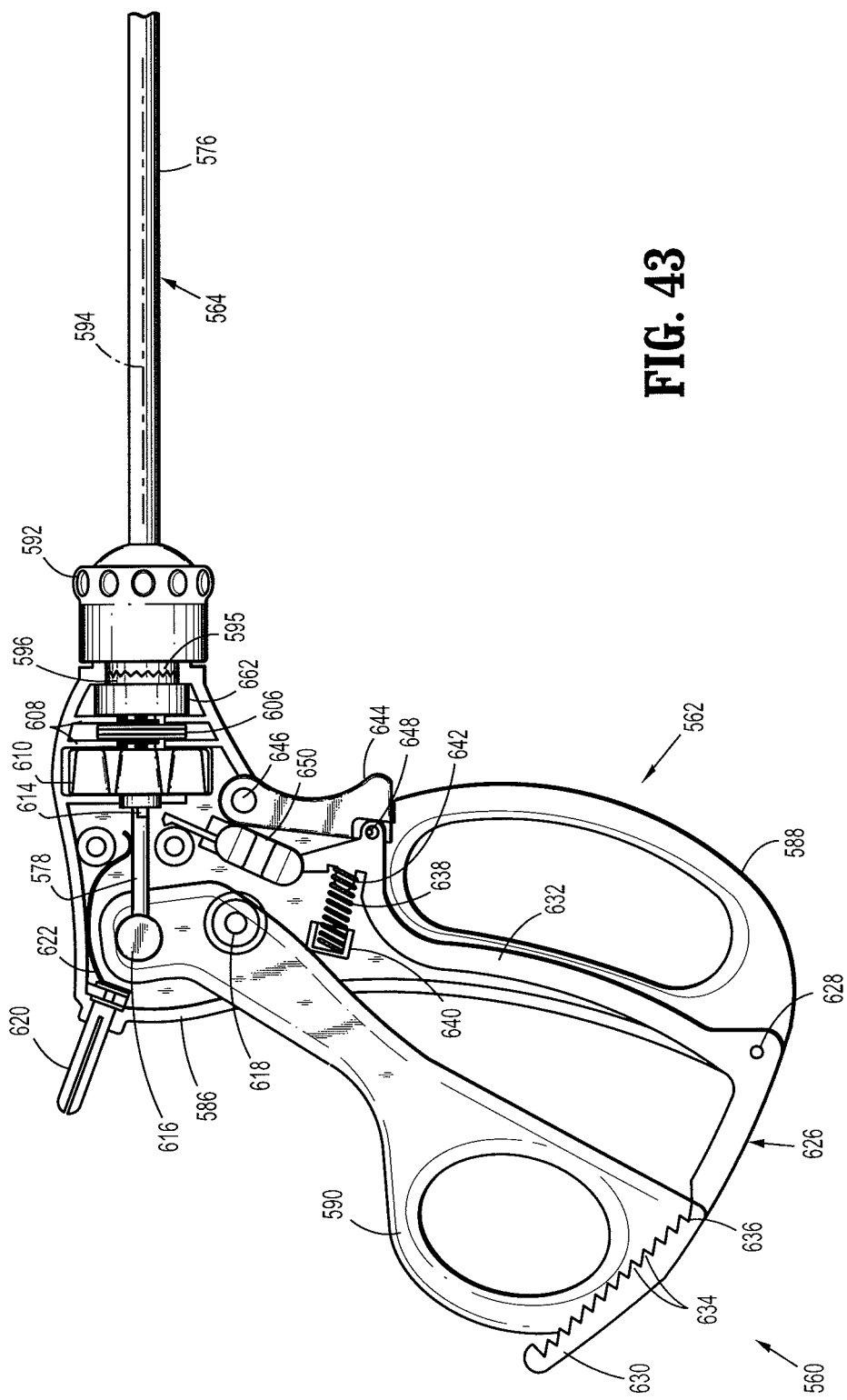
FIG. 43 is a longitudinal cross-sectional view of the handle portion of FIG. 42.

FIGS. 39-41 depict a distal end portion of another embodiment of a laparoscopic instrument, designated by reference numeral 560, while FIGS. 42 and 43 illustrate a handle and actuator assembly 562 at a proximal end of the instrument. The instrument 560 is preferably disposable. As shown in FIGS. 39 and 40, instrument 560 includes a shaft 564 and an operative tip or end effector 566 disposed at the distal end of the shaft. End effecter 566 exemplarily includes a pair of grasper jaws 568 pivotably connected via a pivot pin 570 to one another and to a rigid clevis member 572. Clevis 572 in turn carries an annular coupling element 574 (FIG. 41). The coupling element is fixed to a proximal side of clevis 512 and is rotatably attached to a distal tip of a tubular sheath member 576 that forms an outer part of instrument shaft 504.

Coupling element 574 has a pair of terminal annular flanges 565' and 565" that define an annular groove 567 (FIG. 41). Sheath member 576 is punched in at 569 to form a tooth 571 (FIGS. 39 and 40) that extends into groove 567 and contacts a distally facing transverse surface (not separately designated) of flange 565' to thereby prevent a distal displacement of clevis 572 and end effecter 566 relative to sheath member 576. A proximal displacement of clevis 572 and end effecter 566 relative to sheath member 576 is arrested by an annular shoulder 573 of clevis 572, which abuts the transverse distal end face (not separately designated) of sheath member 576. Clevis 572 is thus translationally fixed to sheath member 576.

Figure 39A:
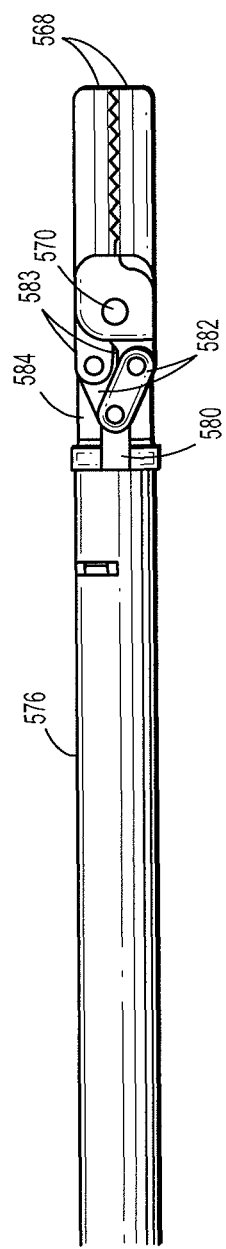
FIG. 39A is a side elevational view similar to FIG. 39 but partially broken away in cross-section.

A partially flexible shifter member 578 (FIG. 41), positioned within shaft 564, is connected at a distal end to a rigid rod 580 via a sleeve 581. Shifter member 578 and rod 580 are inserted into opposite ends of sleeve 581 and may be fastened thereto by crimping, braising, ultrasonic welding, adhesive or any other suitable technique. Rod 580 extends from sleeve 581 through coupling element 574 and a rear end portion of clevis 572 and pivotably connects via a pair of links 582 (see FIG. 39A) to rear or proximal end plates 583 of jaws 568 in a space (not labeled) between two prongs 584 of clevis 572. A longitudinal motion of shifter member 578 and rod 580 relative to sheath member 576, coupling element 574 and clevis 572 induces jaws 568 to turn about pivot pin 570. Rod 580 is rotatably entrained to clevis 572 via jaws 568 and pivot pin 570, so that a rotation of shifter member 578 and rod 580 relative to sheath member 576 rotates jaws 568, clevis 572, and coupling element 574 relative to the sheath member.

Figure 48:
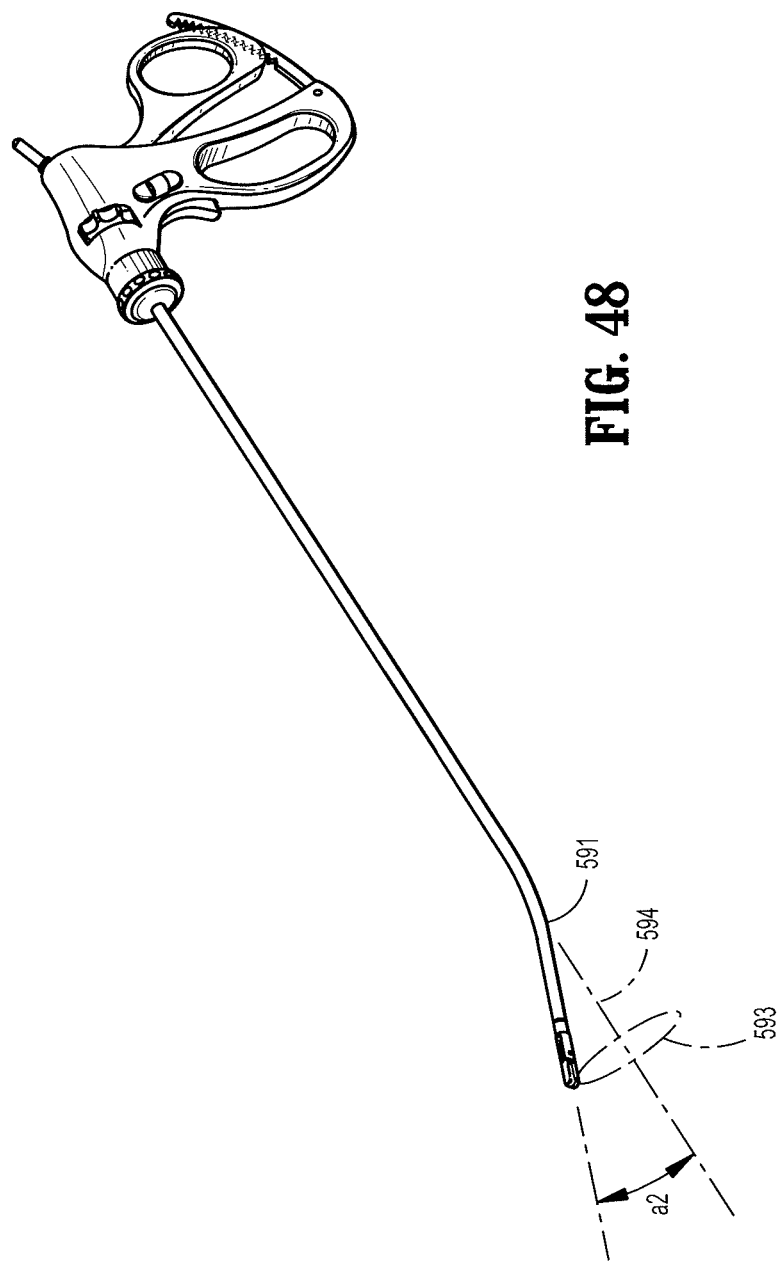
FIG. 48 is a perspective view of the entire instrument of FIGS. 39-47, showing a bend at the distal end of the instrument shaft.

As illustrated in FIGS. 42 and 43, handle and actuator assembly 562 includes a housing 586 with an integral finger grip handle 588 and further includes a thumb ring handle 590 that is pivotably connected to the housing. A first rotary knob 592 on housing 586 is used for rotating sheath member 576 and accordingly shaft 564 about a longitudinal axis 594 of the shaft at the handle and actuator assembly 562. Shaft 564 includes a hockey-stick-type bend 591 so that axis 612 of the distal end portion of shaft 564 is disposed at an acute angle a2 relative to axis 594, as depicted in FIG. 48. (Shifter member 578 is preferably flexible only in a region about the bend 591, to enable a negotiation of the bend in the substantially rigid sheath member 576 by the shifter member.) Accordingly, a turning of knob 592 moves operative tip or end effecter 566 along a circular arc 593 about axis 594. Rotary knob 592 is automatically locked at a desired angular position or orientation, the knob being releasable by pulling it in a distal direction away from handle housing 586 in opposition to a force exerted by a helical biasing spring 596 (FIGS. 45 and 46) tending to pull knob 592 in a proximal direction onto handle housing 586.

Figure 45:
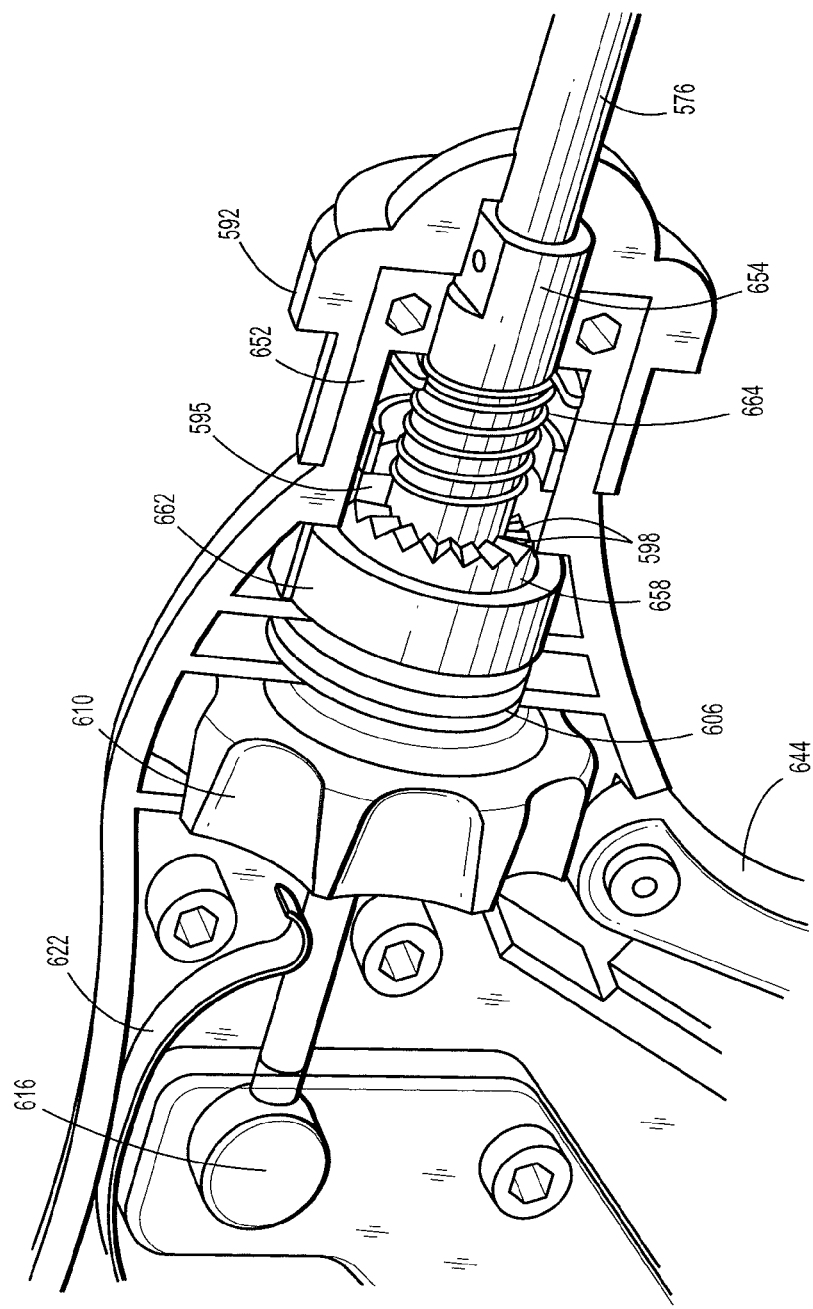
FIG. 45 is a partial front perspective view with select internal components in cross-section and with a housing half-shell removed, of the handle of FIGS. 42-44.
Figure 46:
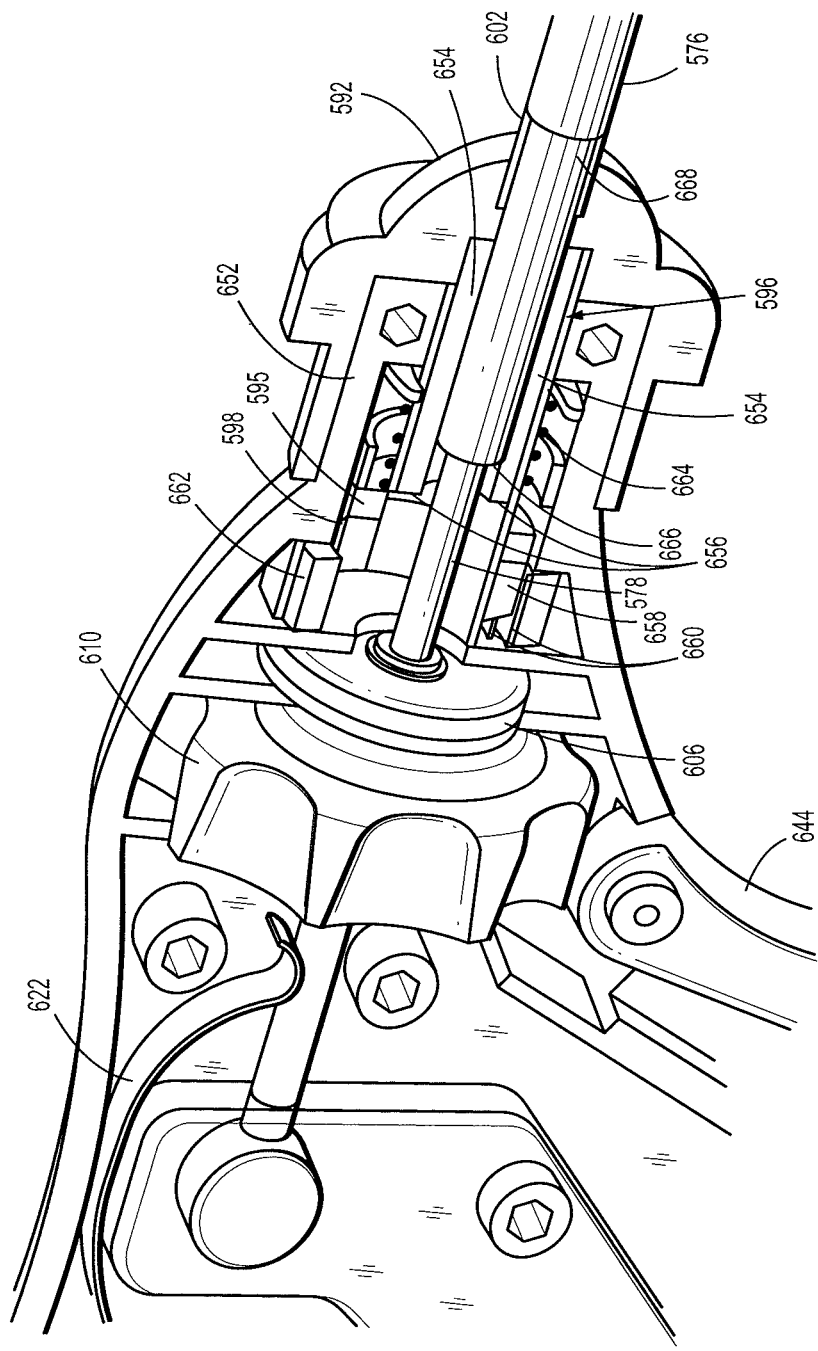
FIG. 46 is a view similar to FIG. 45, showing further parts in cross-section.

As depicted particularly in FIGS. 45 and 46, knob 592 is slidably disposed on a nose portion 652 of handle housing 586. Knob 592 is connected, via a pin (not shown) inserted into a channel 654, to a locking member 596 that is slidably connected to sheath member 576 and rotationally entrained thereto. Specifically, locking member 596 includes a tubular shaft portion 654 with a pair of diametrically opposed longitudinal ribs 656 that extend into respective slots (not designated) on sheath member 576. The slots are defined by two arcuate prongs 602 (only one shown in FIG. 46) at the proximal end of sheath member 576.

Locking member 596 further includes an enlarged proximal terminus 658 with external teeth (not shown) that cooperate with internal teeth 660 on a fixed ring 662 (fixed relative to handle housing 586) to lock knob 592 and sheath member 576 and prevent their rotation relative to housing 586). In order to ensure proper alignment of locking member 596 with fixed ring 662, an alignment ring 595 is disposed inside housing nose 652 about shaft portion 654 of locking member 596. Alignment ring 595 and locking member 596 each have eighteen or some other number of teeth 598 that cooperate to position locking member at any one of either (or so) angular positions about axis 594, the permissible angular positions being aligned with the 18 (or some other number of) internal teeth 660 of fixed ring 662. Locking member 596 and alignment ring 595 are biased into toothed engagement with one another by a helical compression spring 664 disposed about locking member shaft 654 and inside housing nose 652. Alignment ring 595 is rotationally keyed to housing nose 652 so that a rotation of locking member 596 by knob 592 causes the ring to temporarily move distally against the action of spring 664 and then to pop back in the proximal direction at the next permissible angular position defined by teeth 598.

Compression spring 664 also biases both locking member 596 and alignment ring 595 in the proximal direction to maintain locking member in a locked rotational position inside fixed ring 662.

Thus, as knob 592 is pulled in a distal direction, locking member 596 is pulled out of engagement with fixed ring 662, against the action of compression spring 664, enabling the user to turn knob 592 about shaft axis 594. As knob 592 is turned, locking member 596 is impelled into a series of discrete positions defined by alignment ring 595, each position corresponding to a permissible orientation of locking member 596 relative to fixed ring 662. Upon a release of knob 592, locking member 596 slides back into engagement with fixed ring 662.

As shown in FIG. 46, shifter member 578 has a step down 666 from a larger diameter portion 668.

Referring to FIG. 46, prongs 602 of sheath member 576 traverse respective generally C-shaped apertures (not shown) in knob 592, thereby enabling a rotational entrainment and yet a sliding coupling of sheath member 576 to knob 592. Sheath member 576 is fixed against translational movement relative to housing 586 by a pair of C-shaped locking rings 604 that register with circumferential grooves (not shown) in outer surfaces of sheath prongs 602 and are disposed on opposite sides of a disk 606 disposed between two annular partitions 608 integrally molded with and disposed inside housing 586.

Figure 44:
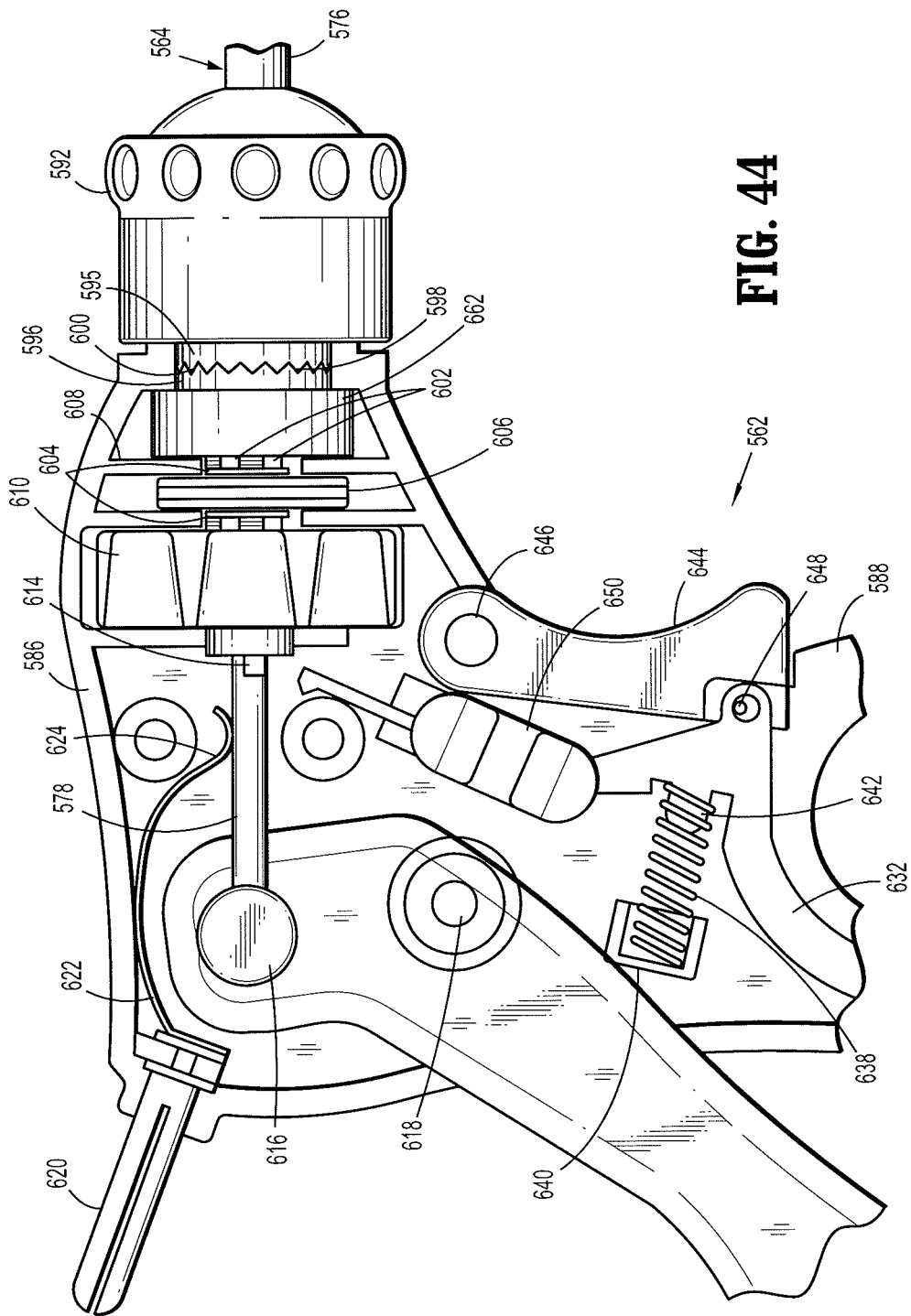
FIG. 44 is a partial longitudinal cross-sectional view similar to that of FIG. 43, but on a larger scale.

As further illustrated in FIGS. 42-44, handle and actuator assembly 562 includes a second rotary knob 610 for rotating operative tip or end effecter 566 about a longitudinal axis 612 of a distal end portion (FIGS. 39, 40) of shaft 564. To that end rotary knob 610 is rotationally entrained to a proximal end of shifter member 578 (FIGS. 43 and 44). Specifically, shifter member 578, which is a substantially rigid rod proximal of the hockey-stick bend in shaft 564, is provided along a proximal end portion with a flat surface 614 to assume a D-shaped cross-section. The D-shaped section of shifter member 578 passes through a D-shaped aperture (not shown) in rotary knob 610, whereby knob 610 is rotationally entrained to shifter member 578. Flat surface 614 extends along a sufficient length of shifter member 578 to enable a limited relative longitudinal shifting of the rod through knob 610, to accommodate motion sufficient to operate jaws 568.

Figure 47:
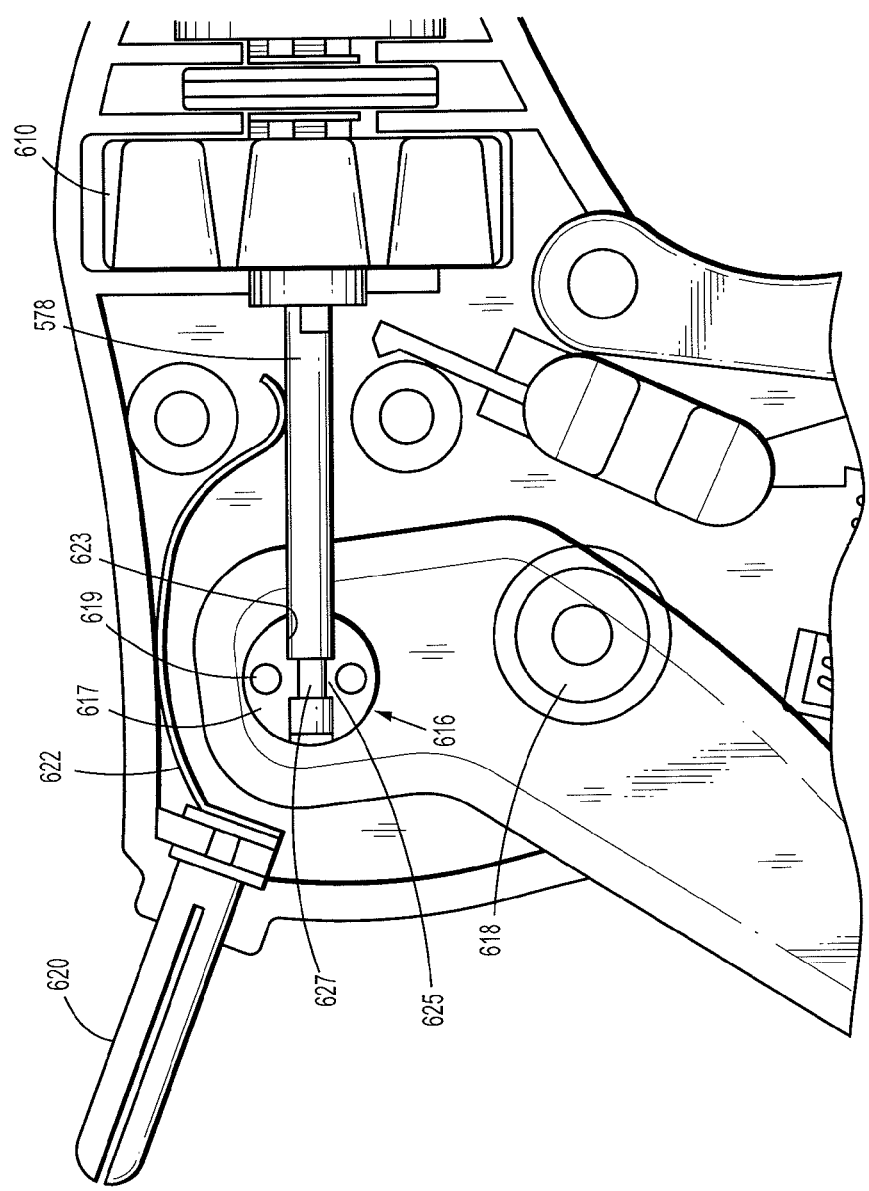
FIG. 47 is a partial longitudinal cross-sectional view similar to that of FIGS. 43 and 44, but on an even larger scale.

At a proximal terminus, shifter member 578 is linked to thumb ring handle 590 via a hollow cylindrical anchor 616. As shown in FIG. 47, anchor 616 comprises a pair of disks 617 (only one shown) assembled to one another via mating pins 619 and holes 621. Disks 617 cooperate to define a through hole 623 with an inwardly projecting annular stop 625 defining a central neck portion (not separately labeled). Shifter member 578 is formed at is proximal terminus with a circumferential groove 627 that receives neck portion 625 so to enable free rotation of shifter member 578 about longitudinal axis 594 of shaft 564. Shifter member 578 extends into handle 590 via a slot 629 therein. Slot 629 accommodates the relative motion of shifter member 578 and handle 590 as the handle pivots about a pin 618.

Anchor 616, ensconced in an upper end of thumb ring handle 590 and revolving about pin 618 when the handle pivots about the pin, moves shifter member 578 alternately in a distal and a proximal direction, depending on the direction of rotation of thumb ring handle 590. That is, the jaws 568 are normally in the closed position. To open the jaws, handle 590 is pivoted toward stationary handle 598, thereby pulling the shifter member 578 proximally.

In the embodiments described herein both jaws are movable to open and close the jaws. However, it is also contemplate that alternatively one jaw can be fixed and the other jaw movable with respect to the other jaw between and open and closed position.

An electrocautery current may be conveyed through shifter member 578 and from thence to jaws 568 via a slotted connecting lug 620 fixed to housing 586 and via a leaf spring 622 with a curved end 624 in sliding contact with shifter member 578.

Handle and actuator assembly 562 includes an L-shaped ratchet member 626 that enables an automatic locking of jaws 568 in a succession of ever more closed configurations during a squeezing of thumb ring handle 590 towards finger grip handle 588. Ratchet member 626 is pivotably mounted to finger grip handle 588 at a pin 628 and includes a first leg 630 extending along a lower edge of thumb ring handle 590 and a second leg 632 extending inside the finger grip handle. Leg 630 is formed along an upper edge with a series of teeth 634 that cooperate with a locking pin 636 on thumb ring handle 590 to prevent a separation of thumb ring handle 590 from finger grip handle 588. Ratchet member 626 is spring biased to push leg 630 towards locking pin 636. The biasing is implemented by a helical compression spring 638 seated at one end in a cup-shaped holder 640 on finger grip handle 588 and at an opposite end on a projection 642 on ratchet leg 632.

Jaws 568 are released from any locked position by pressing a trigger 644 on finger grip handle 588. Trigger 644 is pivotably mounted to finger grip handle 588 via a pin 646 and is pivotably linked to ratchet member 626 via another pin 648. Pressing of trigger 644 moves teeth 634 out of engagement with locking pin 636.

Ratchet member 626 may be deactivated by moving a slider 650 (in a direction toward the ratchet) so that it engages an upper end of ratchet arm 632 and pushes the ratchet member in a counter-clockwise direction (as seen in the drawing), further compressing spring 638 and bringing teeth 634 out of engagement with locking pin 636.

The instruments have been described herein for use through a cannula assembly inserted into the umbilicus of a patient to perform a surgical procedure, such as a cholecystectomy, through a single incision. However, the surgical access ports and the instrumentation can also be used for performance of surgical procedures through single incisions other than through the umbilicus. Moreover, in addition to laparoscopic procedures, the instruments (and ports) can be used for thoracoscopic procedures or other endoscopic or minimally invasive procedures.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An instrument holder assembly for laparoscopic surgical operations,
    said instrument holder assembly having an insertion configuration for at least partial insertion of said instrument holder assembly through an incision at an operative site, and
    an in use configuration for use of said instrument holder assembly for access to said operative site, said instrument holder assembly comprising:
    a flexible member having a surrounding edge;
    an at least partially flexible wall surrounding said flexible member, said at least partially flexible wall being connected to said flexible member all along said surrounding edge, said at least partially flexible wall having a longitudinal axis, said flexible member extending substantially transversely to said longitudinal axis, said at least partially flexible wall extending away from said flexible member at least in a direction away from the operative site; and
    a plurality of cannulas connected to and extending from said flexible member inside said at least partially flexible wall, said plurality of cannulas defining a plurality of separate and mutually spaced apertures for receiving respective elongate laparoscopic surgical members, a first cannula of the plurality of cannulas being movable with respect to a second cannula of the plurality of cannulas;
    wherein, for the insertion configuration, the flexible member and the at least partially flexible wall are folded into a compact configuration wherein the at least partially flexible wall has a compressible cross-sectional dimension, said compressible cross-sectional dimension along the longitudinal axis of said at least partially flexible wall being less than a dimension of the incision at the operative site where said at least partially flexible wall extends at least partially through the incision, and
    wherein during the in use configuration, the first cannula configured to receive a first curved instrument having a handle, a shaft and first and second jaws, the first and second jaws being rotatable relative to the shaft and the shaft being rotatable relative to the handle; and
    the second cannula configured to receive a second curved instrument having a handle, a shaft and third and fourth jaws, the third and fourth jaws being rotatable relative to the shaft and the shaft being rotatable relative to the handle.

2. The instrument holder assembly defined in claim 1, wherein said flexible member and said at least partially flexible wall each have a height dimension extending parallel to said longitudinal axis, the height dimension of said at least partially flexible wall being substantially greater than the height dimension of said flexible member.

3. The instrument holder assembly defined in claim 1, wherein said at least partially flexible wall has at least one end portion extending as a flange to said flexible member on a side of said flexible member opposite the operative site.

4. The instrument holder assembly defined in claim 3, wherein the at least partially flexible wall is substantially rigid in a region about the flexible member and flexible at least in a distal region of the at least partially flexible wall.

5. The instrument holder assembly defined in claim 4, configured wherein, when the instrument holder assembly is in the in use configuration, the distal region of the at least partially flexible wall is inside the incision at the operative site.

6. The instrument holder assembly defined in claim 1, wherein said flexible member is located at one end of said at least partially flexible wall.

7. The instrument holder assembly defined in claim 1, wherein said flexible member and said at least partially flexible wall form two cup shapes.

8. The instrument holder assembly defined in claim 1, wherein said at least partially flexible wall has a first inner diameter at said flexible member and a second inner diameter at an end opposite said flexible member, said second inner diameter being larger than said first inner diameter.

9. The instrument holder assembly defined in claim 1, wherein the instrument holder assembly consists of said flexible member and said at least partially flexible wall.

10. The instrument holder assembly defined in claim 1, wherein said apertures have a longitudinal dimension extending generally parallel to said axis, at least one of said apertures having a curvilinear or arced shape along the longitudinal dimension of said one of said apertures.

11. The instrument holder assembly defined in claim 1, wherein said at least partially flexible wall is at least partially curved in a direction in line with said longitudinal axis.

12. The instrument holder assembly defined in claim 1, wherein said at least partially flexible wall is provided with an anchoring element for securing the instrument holder assembly adjacent the operative site, said anchoring element being taken from the group consisting of a hook and an eyelet.

13. The instrument holder assembly defined in claim 1, wherein said plurality of cannulas all extend in a common direction away from said flexible member so that said cannulas are all disposed on only one side of said flexible member.

14. The instrument holder assembly defined in claim 1, wherein the instrument holder assembly is inflatable and deflatable.

15. The instrument holder assembly defined in claim 14, wherein the instrument holder assembly is inflated when in the insertion configuration to assume the in use configuration.

16. The instrument holder assembly defined in claim 1, wherein said at least partially flexible wall extending away from said flexible member at least in a direction away from the operative site thereby defines together with said flexible member, in the in use configuration, a cup shape on a side of said flexible member.

17. The instrument holder assembly defined in claim 16, wherein the first curved instrument includes a jaw actuating mechanism to move the first and second jaws between open and closed positions.

18. The instrument holder assembly defined in claim 17, wherein the second curved instrument includes a jaw actuating mechanism to move the third and fourth jaws between the open and closed positions.

\* \* \* \* \*